(12) United States Patent
Tran et al.

(10) Patent No.: US 11,759,618 B2
(45) Date of Patent: Sep. 19, 2023

(54) BLOOD CONTROL FOR A CATHETER INSERTION DEVICE

(71) Applicant: C. R. Bard, Inc., Franklin Lakes, NJ (US)

(72) Inventors: Huy N. Tran, Riverton, UT (US); Mark A. Christensen, Salt Lake City, UT (US); Chad A. Hadley, North Salt Lake, UT (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 663 days.

(21) Appl. No.: 16/696,844

(22) Filed: Nov. 26, 2019

(65) Prior Publication Data
US 2020/0094037 A1     Mar. 26, 2020

Related U.S. Application Data

(62) Division of application No. 15/702,537, filed on Sep. 12, 2017, now Pat. No. 10,493,262.
(Continued)

(51) Int. Cl.
*A61M 39/22*     (2006.01)
*A61M 25/00*     (2006.01)
(Continued)

(52) U.S. Cl.
CPC ...... *A61M 39/221* (2013.01); *A61M 25/0097* (2013.01); *A61M 25/065* (2013.01);
(Continued)

(58) Field of Classification Search
CPC .... A61M 39/221; A61M 39/24; A61M 39/10; A61M 25/09041; A61M 25/0693;
(Continued)

(56) References Cited

U.S. PATENT DOCUMENTS 2,211,975 A    8/1940   Hendrickson
2,259,488 A   10/1941   Raiche
(Continued)

FOREIGN PATENT DOCUMENTS

AU    691141 B2    5/1998
AU    710967 B2    9/1999
(Continued)

OTHER PUBLICATIONS

U.S. Appl. No. 15/869,872, filed Jan. 12, 2018 Notice of Allowance dated Dec. 24, 2021.
(Continued)

*Primary Examiner* — Nathan R Price
*Assistant Examiner* — Mark A Igel
(74) *Attorney, Agent, or Firm* — Rutan & Tucker LLP

(57) ABSTRACT

A fluid control component configured for controlling fluid flow through the hub of a catheter assembly during and after placement into the patient is disclosed. In one embodiment, the fluid control component comprises a body disposed within a cavity of the hub, the body being movable between a first position and a second position, wherein the body does not pierce a valve disposed in the hub when in the first position and wherein the body pierces the valve when in the second position. The body includes a conduit to enable fluid flow through an internal portion of the body when the body is in the second position, and a plurality of longitudinally extending ribs disposed on an exterior surface of the body. The ribs provide at least one fluid flow channel between the valve and an external portion of the body when the body is in the second position.

8 Claims, 11 Drawing Sheets

Related U.S. Application Data

(60) Provisional application No. 62/393,531, filed on Sep. 12, 2016.

(51) Int. Cl.
*A61M 25/06* (2006.01)
*A61M 39/24* (2006.01)
*A61M 25/09* (2006.01)
*A61M 39/10* (2006.01)

(52) U.S. Cl.
CPC ......... *A61M 39/24* (2013.01); *A61M 25/0606* (2013.01); *A61M 25/0631* (2013.01); *A61M 25/0693* (2013.01); *A61M 25/09041* (2013.01); *A61M 39/10* (2013.01); *A61M 2039/2426* (2013.01); *A61M 2207/00* (2013.01)

(58) Field of Classification Search
CPC .......... A61M 25/0631; A61M 25/0606; A61M 25/065; A61M 25/0097; A61M 2039/2426; A61M 2207/00
See application file for complete search history.

(56) References Cited

U.S. PATENT DOCUMENTS

| | | | |
|---|---|---|---|
| 2,330,400 A | 9/1943 | Winder | |
| D138,589 S | 8/1944 | Brandenburg | |
| 3,185,151 A | 5/1965 | Czomy | |
| 3,297,030 A | 1/1967 | Czomy et al. | |
| 3,416,567 A | 12/1968 | von Dardel et al. | |
| 3,469,579 A | 9/1969 | Hubert | |
| 3,500,828 A | 3/1970 | Podhora | |
| 3,552,384 A | 1/1971 | Pierie et al. | |
| 3,572,334 A | 3/1971 | Petterson | |
| 3,585,996 A | 6/1971 | Reynolds et al. | |
| 3,589,361 A | 6/1971 | Loper et al. | |
| 3,592,192 A | 7/1971 | Harautuneian | |
| 3,595,230 A | 7/1971 | Suyeoka et al. | |
| 3,610,240 A | 10/1971 | Harautuneian | |
| 3,682,173 A | 8/1972 | Center | |
| 3,766,916 A | 10/1973 | Moorehead et al. | |
| 3,884,242 A | 5/1975 | Bazell et al. | |
| 3,921,631 A | 11/1975 | Thompson | |
| 3,995,628 A | 12/1976 | Gula et al. | |
| 4,027,668 A | 6/1977 | Dunn | |
| 4,037,600 A | 7/1977 | Poncy et al. | |
| 4,079,738 A | 3/1978 | Dunn et al. | |
| 4,106,506 A | 8/1978 | Koehn et al. | |
| 4,177,809 A | 12/1979 | Moorehead | |
| 4,292,970 A | 10/1981 | Hession, Jr. | |
| 4,317,445 A | 3/1982 | Robinson | |
| 4,345,602 A | 8/1982 | Yoshimura et al. | |
| 4,354,491 A | 10/1982 | Marbry | |
| 4,368,730 A | 1/1983 | Sharrock | |
| 4,387,879 A * | 6/1983 | Tauschinski | A61M 39/0693 604/249 |
| 4,417,886 A | 11/1983 | Frankhouser et al. | |
| 4,449,693 A | 5/1984 | Gereg | |
| 4,456,017 A | 6/1984 | Miles | |
| 4,464,171 A | 8/1984 | Garwin | |
| 4,509,534 A | 4/1985 | Tassin, Jr. | |
| 4,509,945 A | 4/1985 | Kramann et al. | |
| 4,511,359 A | 4/1985 | Vaillancourt | |
| 4,512,766 A | 4/1985 | Vailancourt | |
| 4,525,157 A | 6/1985 | Vaillancourt | |
| 4,581,019 A | 4/1986 | Curelaru et al. | |
| 4,585,440 A | 4/1986 | Tchervenkov et al. | |
| D287,877 S | 1/1987 | Holewinski et al. | |
| 4,728,322 A | 3/1988 | Walker et al. | |
| 4,738,659 A | 4/1988 | Sleiman | |
| 4,747,831 A | 5/1988 | Kulli | |
| 4,767,407 A | 8/1988 | Foran | |
| 4,772,264 A | 9/1988 | Cragg | |
| 4,772,267 A | 9/1988 | Brown | |
| 4,781,703 A | 11/1988 | Walker et al. | |
| 4,792,531 A | 12/1988 | Kakihana | |
| 4,798,193 A | 1/1989 | Giesy et al. | |
| 4,813,934 A | 3/1989 | Engelson et al. | |
| 4,826,070 A | 5/1989 | Kakihana | |
| 4,828,547 A | 5/1989 | Sahi et al. | |
| 4,834,708 A | 5/1989 | Pillari | |
| 4,834,718 A | 5/1989 | McDonald | |
| 4,840,613 A | 6/1989 | Balbierz | |
| 4,840,622 A | 6/1989 | Hardy | |
| 4,842,591 A * | 6/1989 | Luther | A61M 39/26 604/905 |
| 4,846,812 A | 7/1989 | Walker et al. | |
| 4,850,961 A | 7/1989 | Wanderer et al. | |
| 4,860,757 A | 8/1989 | Lynch et al. | |
| 4,869,259 A | 9/1989 | Elkins | |
| D304,079 S | 10/1989 | McFarlane | |
| 4,871,358 A | 10/1989 | Gold | |
| 4,874,377 A | 10/1989 | Newgard et al. | |
| 4,883,461 A | 11/1989 | Sawyer | |
| 4,883,699 A | 11/1989 | Aniuk et al. | |
| 4,894,052 A | 1/1990 | Crawford | |
| 4,895,346 A | 1/1990 | Steigerwald | |
| 4,900,307 A | 2/1990 | Kulli | |
| 4,906,956 A | 3/1990 | Kakihana | |
| 4,908,021 A | 3/1990 | McFarlane | |
| 4,909,793 A | 3/1990 | Vining et al. | |
| 4,911,691 A | 3/1990 | Aniuk et al. | |
| 4,913,704 A | 4/1990 | Kurimoto | |
| 4,917,102 A | 4/1990 | Miller et al. | |
| 4,917,668 A * | 4/1990 | Haindl | F16L 37/38 604/167.03 |
| 4,917,671 A | 4/1990 | Chang | |
| 4,929,235 A | 5/1990 | Merry et al. | |
| 4,935,010 A | 6/1990 | Cox et al. | |
| 4,944,725 A | 7/1990 | McDonald | |
| 4,944,728 A | 7/1990 | Carrell et al. | |
| 4,955,863 A | 9/1990 | Walker et al. | |
| 4,961,729 A | 10/1990 | Vaillancourt | |
| 4,966,586 A * | 10/1990 | Vaillancourt | A61M 25/0606 604/122 |
| 4,966,589 A | 10/1990 | Kaufman | |
| 4,994,042 A | 2/1991 | Vadher | |
| 4,994,047 A | 2/1991 | Walker et al. | |
| 4,995,866 A | 2/1991 | Amplatz et al. | |
| 5,007,901 A | 4/1991 | Shields | |
| 5,009,642 A | 4/1991 | Sahi | |
| 5,019,048 A | 5/1991 | Margolin | |
| 5,019,049 A | 5/1991 | Haining | |
| D318,733 S | 7/1991 | Wyzgala | |
| 5,034,347 A | 7/1991 | Kakihana | |
| 5,047,013 A | 9/1991 | Rossdeutscher | |
| D321,250 S | 10/1991 | Jepson et al. | |
| 5,053,014 A | 10/1991 | Van Heugten | |
| 5,054,501 A | 10/1991 | Chuttani et al. | |
| 5,061,254 A | 10/1991 | Karakelle et al. | |
| 5,064,416 A | 11/1991 | Newgard et al. | |
| 5,078,694 A | 1/1992 | Wallace | |
| 5,078,696 A | 1/1992 | Nedbaluk | |
| 5,078,702 A | 1/1992 | Pomeranz | |
| 5,084,023 A | 1/1992 | Lemieux | |
| 5,085,645 A | 2/1992 | Purdy et al. | |
| 5,088,984 A | 2/1992 | Fields | |
| 5,093,692 A | 3/1992 | Su et al. | |
| 5,098,392 A | 3/1992 | Fleischhacker et al. | |
| 5,098,395 A | 3/1992 | Fields | |
| 5,098,396 A * | 3/1992 | Taylor | A61M 39/0613 604/167.03 |
| 5,098,405 A | 3/1992 | Peterson et al. | |
| 5,108,375 A | 4/1992 | Harrison et al. | |
| 5,108,376 A | 4/1992 | Bonaldo | |
| 5,112,312 A | 5/1992 | Luther | |
| 5,116,323 A | 5/1992 | Kreuzer et al. | |
| 5,120,317 A | 6/1992 | Luther | |
| 5,125,906 A | 6/1992 | Fleck | |
| 5,135,487 A | 8/1992 | Morrill et al. | |
| 5,137,515 A | 8/1992 | Hogan | |
| 5,149,326 A | 9/1992 | Woodgrift et al. | |
| 5,154,703 A | 10/1992 | Bonaldo | |

(56) References Cited

U.S. PATENT DOCUMENTS

| | | | |
|---|---|---|---|
| 5,156,590 A | 10/1992 | Vilmar | |
| 5,156,596 A | 10/1992 | Balbierz et al. | |
| 5,158,544 A | 10/1992 | Weinstein | |
| 5,167,637 A * | 12/1992 | Okada | A61M 39/0606 604/167.04 |
| 5,176,650 A | 1/1993 | Haining | |
| 5,186,168 A | 2/1993 | Spofford et al. | |
| 5,186,712 A | 2/1993 | Kelso et al. | |
| 5,188,607 A | 2/1993 | Wu | |
| 5,190,528 A | 3/1993 | Fonger et al. | |
| 5,192,301 A | 3/1993 | Kamiya et al. | |
| 5,195,974 A | 3/1993 | Hardy | |
| 5,195,980 A | 3/1993 | Catlin | |
| 5,195,985 A | 3/1993 | Hall | |
| 5,205,830 A | 4/1993 | Dassa et al. | |
| 5,215,527 A | 6/1993 | Beck et al. | |
| 5,215,528 A | 6/1993 | Purdy et al. | |
| 5,217,435 A | 6/1993 | Kring | |
| 5,219,335 A | 6/1993 | Willard et al. | |
| 5,221,255 A | 6/1993 | Mahurkar et al. | |
| 5,222,944 A | 6/1993 | Harris | |
| 5,225,369 A | 7/1993 | Su et al. | |
| 5,226,899 A | 7/1993 | Lee et al. | |
| D338,955 S | 8/1993 | Gresl et al. | |
| 5,234,410 A | 8/1993 | Graham et al. | |
| 5,242,411 A | 9/1993 | Yamamoto et al. | |
| 5,246,426 A | 9/1993 | Lewis et al. | |
| 5,246,430 A | 9/1993 | MacFarlane | |
| 5,254,107 A | 10/1993 | Soltesz | |
| 5,257,980 A | 11/1993 | Van Antwerp et al. | |
| 5,267,982 A | 12/1993 | Sylvanowicz | |
| 5,269,771 A | 12/1993 | Thomas et al. | |
| D345,419 S | 3/1994 | Horrigan et al. | |
| 5,290,310 A | 3/1994 | Makower et al. | |
| 5,297,546 A | 3/1994 | Spofford et al. | |
| 5,312,359 A | 5/1994 | Wallace | |
| 5,312,361 A | 5/1994 | Zadini et al. | |
| 5,312,363 A * | 5/1994 | Ryan | A61M 39/06 604/167.04 |
| 5,320,608 A | 6/1994 | Gerrone | |
| 5,322,517 A | 6/1994 | Sircom et al. | |
| 5,330,435 A | 7/1994 | Vaillancourt | |
| 5,334,159 A | 8/1994 | Turkel | |
| 5,338,311 A | 8/1994 | Mahurkar | |
| 5,352,205 A | 10/1994 | Dales et al. | |
| 5,358,796 A | 10/1994 | Nakamura et al. | |
| 5,366,441 A | 11/1994 | Crawford | |
| 5,368,661 A | 11/1994 | Nakamura et al. | |
| D353,668 S | 12/1994 | Banks et al. | |
| 5,376,082 A | 12/1994 | Phelps | |
| 5,376,094 A | 12/1994 | Kline | |
| 5,380,290 A | 1/1995 | Makower et al. | |
| 5,380,292 A | 1/1995 | Wilson | |
| 5,395,341 A | 3/1995 | Slater | |
| 5,397,311 A | 3/1995 | Walker et al. | |
| 5,405,323 A | 4/1995 | Rogers et al. | |
| 5,415,177 A | 5/1995 | Zadini et al. | |
| 5,415,645 A | 5/1995 | Friend et al. | |
| 5,419,766 A | 5/1995 | Chang et al. | |
| 5,419,777 A | 5/1995 | Hofling | |
| 5,423,760 A | 6/1995 | Yoon | |
| 5,425,718 A | 6/1995 | Tay et al. | |
| 5,431,506 A | 7/1995 | Masunaga | |
| 5,439,449 A | 8/1995 | Mapes et al. | |
| 5,445,625 A | 8/1995 | Voda | |
| 5,454,785 A | 10/1995 | Smith | |
| 5,454,790 A | 10/1995 | Dubrul | |
| 5,456,258 A | 10/1995 | Kondo et al. | |
| 5,456,668 A | 10/1995 | Ogle, II | |
| 5,458,658 A | 10/1995 | Sircom | |
| 5,466,230 A | 11/1995 | Davila | |
| 5,480,389 A | 1/1996 | McWha et al. | |
| 5,482,395 A | 1/1996 | Gasparini | |
| 5,484,419 A | 1/1996 | Fleck | |
| 5,487,734 A | 1/1996 | Thorne et al. | |
| 5,489,273 A | 2/1996 | Whitney et al. | |
| 5,496,281 A | 3/1996 | Krebs | |
| 5,501,671 A | 3/1996 | Rosen et al. | |
| 5,501,675 A | 3/1996 | Erskine | |
| 5,507,300 A | 4/1996 | Mukai et al. | |
| 5,512,052 A | 4/1996 | Jesch | |
| 5,514,108 A | 5/1996 | Stevens | |
| 5,520,655 A | 5/1996 | Davila et al. | |
| 5,520,657 A | 5/1996 | Sellers et al. | |
| D371,195 S | 6/1996 | Krebs | |
| 5,522,807 A | 6/1996 | Luther | |
| 5,527,290 A | 6/1996 | Zadini et al. | |
| 5,527,291 A | 6/1996 | Zadini et al. | |
| 5,531,701 A | 7/1996 | Luther | |
| 5,531,713 A | 7/1996 | Mastronardi et al. | |
| 5,533,988 A | 7/1996 | Dickerson et al. | |
| 5,535,785 A * | 7/1996 | Werge | F16K 15/1825 251/149.6 |
| 5,542,933 A | 8/1996 | Marks | |
| 5,554,136 A | 9/1996 | Luther | |
| 5,562,629 A | 10/1996 | Haughton et al. | |
| 5,562,630 A | 10/1996 | Nichols | |
| 5,562,631 A | 10/1996 | Bogert | |
| 5,562,633 A | 10/1996 | Wozencroft | |
| 5,562,634 A | 10/1996 | Flumene et al. | |
| 5,569,202 A | 10/1996 | Kovalic et al. | |
| 5,569,217 A | 10/1996 | Luther | |
| 5,571,073 A | 11/1996 | Castillo | |
| 5,573,510 A | 11/1996 | Isaacson | |
| 5,575,777 A | 11/1996 | Cover et al. | |
| 5,591,194 A | 1/1997 | Berthiaume | |
| 5,599,291 A | 2/1997 | Balbierz et al. | |
| 5,599,327 A | 2/1997 | Sugahara et al. | |
| 5,609,583 A | 3/1997 | Hakki et al. | |
| 5,613,663 A | 3/1997 | Schmidt et al. | |
| 5,613,954 A | 3/1997 | Nelson et al. | |
| 5,630,802 A | 5/1997 | Moellmann et al. | |
| 5,630,823 A | 5/1997 | Schmitz-Rode et al. | |
| 5,634,475 A | 6/1997 | Wolvek | |
| 5,634,913 A | 6/1997 | Stinger | |
| 5,637,091 A | 6/1997 | Hakky et al. | |
| 5,645,076 A | 7/1997 | Yoon | |
| 5,651,772 A | 7/1997 | Arett | |
| D383,538 S | 9/1997 | Erskine et al. | |
| 5,662,622 A | 9/1997 | Gore et al. | |
| 5,674,241 A | 10/1997 | Bley et al. | |
| 5,676,658 A | 10/1997 | Erskine | |
| 5,683,368 A | 11/1997 | Schmidt | |
| 5,683,370 A | 11/1997 | Luther et al. | |
| 5,685,855 A | 11/1997 | Erskine | |
| 5,685,858 A | 11/1997 | Kawand | |
| 5,685,860 A | 11/1997 | Chang et al. | |
| 5,688,249 A | 11/1997 | Chang et al. | |
| 5,693,025 A | 12/1997 | Stevens | |
| 5,695,474 A | 12/1997 | Daugherty | |
| 5,697,914 A | 12/1997 | Brimhall | |
| 5,700,250 A | 12/1997 | Erskine | |
| 5,702,367 A | 12/1997 | Cover et al. | |
| 5,702,369 A | 12/1997 | Mercereau | |
| 5,704,914 A * | 1/1998 | Stocking | A61M 25/0631 604/195 |
| 5,722,425 A | 3/1998 | Bostrom | |
| 5,725,503 A | 3/1998 | Arnett | |
| 5,730,150 A | 3/1998 | Peppel et al. | |
| 5,730,733 A | 3/1998 | Mortier et al. | |
| 5,730,741 A | 3/1998 | Horzewski et al. | |
| 5,738,144 A | 4/1998 | Rogers | |
| 5,738,660 A | 4/1998 | Luther | |
| 5,743,882 A | 4/1998 | Luther | |
| 5,743,888 A | 4/1998 | Wilkes et al. | |
| 5,749,371 A | 5/1998 | Zadini et al. | |
| 5,749,857 A | 5/1998 | Cuppy | |
| 5,749,861 A | 5/1998 | Guala et al. | |
| 5,750,741 A | 5/1998 | Crocker et al. | |
| 5,755,693 A | 5/1998 | Walker et al. | |
| 5,755,709 A | 5/1998 | Cuppy | |
| 5,762,630 A | 6/1998 | Bley et al. | |
| 5,762,636 A | 6/1998 | Rupp et al. | |
| 5,765,682 A | 6/1998 | Bley et al. | |

(56) References Cited

U.S. PATENT DOCUMENTS

| | | |
|---|---|---|
| 5,779,679 A | 7/1998 | Shaw |
| 5,779,680 A | 7/1998 | Yoon |
| 5,779,681 A | 7/1998 | Bonn |
| 5,782,807 A | 7/1998 | Falvai et al. |
| D397,434 S | 8/1998 | Pike |
| 5,792,124 A | 8/1998 | Horrigan et al. |
| 5,800,395 A | 9/1998 | Botich et al. |
| 5,807,339 A | 9/1998 | Bostrom et al. |
| 5,807,342 A | 9/1998 | Musgrave et al. |
| 5,807,350 A | 9/1998 | Diaz |
| 5,810,780 A | 9/1998 | Brimhall et al. |
| 5,810,835 A | 9/1998 | Ryan et al. |
| 5,813,411 A | 9/1998 | Van Bladel et al. |
| 5,817,058 A | 10/1998 | Shaw |
| 5,817,069 A | 10/1998 | Arnett |
| 5,824,001 A | 10/1998 | Erskine |
| 5,827,202 A | 10/1998 | Miraki et al. |
| 5,827,221 A | 10/1998 | Phelps |
| 5,827,227 A | 10/1998 | DeLago |
| 5,830,190 A | 11/1998 | Howell |
| 5,830,224 A | 11/1998 | Cohn et al. |
| 5,839,470 A | 11/1998 | Hiejima et al. |
| 5,843,002 A | 12/1998 | Pecor et al. |
| 5,843,038 A | 12/1998 | Bailey |
| 5,846,259 A | 12/1998 | Berthiaume |
| 5,851,196 A | 12/1998 | Arnett |
| 5,853,393 A | 12/1998 | Bogert |
| 5,855,615 A | 1/1999 | Bley et al. |
| 5,858,002 A | 1/1999 | Jesch |
| 5,865,806 A | 2/1999 | Howell |
| 5,873,864 A | 2/1999 | Luther et al. |
| 5,879,332 A | 3/1999 | Schwemberger et al. |
| 5,879,337 A | 3/1999 | Kuracina et al. |
| 5,885,217 A | 3/1999 | Gisselberg et al. |
| 5,885,251 A | 3/1999 | Luther |
| 5,891,098 A | 4/1999 | Huang |
| 5,891,105 A | 4/1999 | Mahurkar |
| 5,895,398 A | 4/1999 | Wensel et al. |
| 5,902,274 A | 5/1999 | Yamamoto et al. |
| 5,902,832 A | 5/1999 | Van Bladel et al. |
| 5,911,705 A | 6/1999 | Howell |
| 5,911,710 A | 6/1999 | Barry et al. |
| 5,913,848 A | 6/1999 | Luther et al. |
| 5,916,208 A | 6/1999 | Luther et al. |
| 5,928,199 A | 7/1999 | Nakagami |
| D413,382 S | 8/1999 | Maissami |
| 5,935,110 A | 8/1999 | Brimhall |
| 5,941,854 A | 8/1999 | Bhitiyakul |
| 5,944,690 A | 8/1999 | Falwell et al. |
| 5,947,930 A | 9/1999 | Schwemberger et al. |
| 5,951,520 A | 9/1999 | Burzynski et al. |
| 5,954,698 A | 9/1999 | Pike |
| 5,957,893 A | 9/1999 | Luther et al. |
| 5,964,744 A | 10/1999 | Balbierz et al. |
| 5,967,490 A | 10/1999 | Pike |
| 5,984,895 A | 11/1999 | Padilla et al. |
| 5,984,903 A | 11/1999 | Nadal |
| 5,989,220 A | 11/1999 | Shaw et al. |
| 5,989,271 A | 11/1999 | Bonnette et al. |
| 5,997,507 A | 12/1999 | Dysarz |
| 5,997,510 A | 12/1999 | Schwemberger |
| 6,001,080 A | 12/1999 | Kuracina et al. |
| 6,004,278 A | 12/1999 | Botich et al. |
| 6,004,294 A | 12/1999 | Brimhall et al. |
| 6,004,295 A | 12/1999 | Langer et al. |
| 6,011,988 A | 1/2000 | Lynch et al. |
| 6,019,736 A | 2/2000 | Avellanet et al. |
| 6,022,319 A | 2/2000 | Willard et al. |
| 6,024,727 A | 2/2000 | Thorne et al. |
| 6,024,729 A * | 2/2000 | Dehdashtian ..... A61M 39/0606 604/167.04 |
| 6,045,734 A | 4/2000 | Luther et al. |
| 6,056,726 A | 5/2000 | Isaacson |
| 6,059,484 A | 5/2000 | Greive |
| 6,066,100 A | 5/2000 | Willard et al. |
| 6,074,378 A | 6/2000 | Mouri et al. |
| 6,077,244 A | 6/2000 | Botich et al. |
| 6,080,137 A | 6/2000 | Pike |
| 6,083,237 A | 7/2000 | Huitema et al. |
| 6,096,004 A | 8/2000 | Meglan et al. |
| 6,096,005 A | 8/2000 | Botich et al. |
| 6,109,264 A | 8/2000 | Sauer |
| 6,117,108 A | 9/2000 | Woehr et al. |
| 6,120,494 A | 9/2000 | Jonkman |
| 6,126,633 A | 10/2000 | Kaji et al. |
| 6,126,641 A | 10/2000 | Shields |
| 6,139,532 A | 10/2000 | Howell et al. |
| 6,139,557 A | 10/2000 | Passafaro et al. |
| 6,159,179 A | 12/2000 | Simonson |
| 6,171,234 B1 | 1/2001 | White et al. |
| 6,171,287 B1 | 1/2001 | Lynn et al. |
| 6,176,842 B1 | 1/2001 | Tachibana et al. |
| 6,193,690 B1 | 2/2001 | Dysarz |
| 6,197,001 B1 | 3/2001 | Wilson et al. |
| 6,197,007 B1 | 3/2001 | Thorne et al. |
| 6,197,041 B1 | 3/2001 | Shichman et al. |
| 6,203,527 B1 | 3/2001 | Zadini et al. |
| 6,213,978 B1 | 4/2001 | Voyten |
| 6,217,558 B1 | 4/2001 | Zadini et al. |
| 6,221,047 B1 | 4/2001 | Greene et al. |
| 6,221,048 B1 | 4/2001 | Phelps |
| 6,221,049 B1 | 4/2001 | Selmon et al. |
| 6,224,569 B1 | 5/2001 | Brimhall |
| 6,228,060 B1 | 5/2001 | Howell |
| 6,228,062 B1 | 5/2001 | Howell et al. |
| 6,228,073 B1 | 5/2001 | Noone et al. |
| 6,245,045 B1 | 6/2001 | Stratienko |
| 6,251,092 B1 | 6/2001 | Qin et al. |
| 6,268,399 B1 | 7/2001 | Hultine et al. |
| 6,270,480 B1 | 8/2001 | Dorr et al. |
| 6,273,871 B1 | 8/2001 | Davis et al. |
| 6,280,419 B1 | 8/2001 | Vojtasek |
| 6,287,278 B1 | 9/2001 | Woehr et al. |
| 6,309,379 B1 | 10/2001 | Willard et al. |
| 6,319,244 B2 | 11/2001 | Suresh et al. |
| 6,322,537 B1 | 11/2001 | Chang |
| D452,003 S | 12/2001 | Niermann |
| 6,325,781 B1 | 12/2001 | Takagi et al. |
| 6,325,797 B1 | 12/2001 | Stewart et al. |
| 6,336,914 B1 | 1/2002 | Gillespie, III |
| 6,352,520 B1 | 3/2002 | Miyazaki |
| 6,368,337 B1 | 4/2002 | Kieturakis et al. |
| 6,379,333 B1 | 4/2002 | Brimhall et al. |
| 6,379,372 B1 | 4/2002 | Dehdashtian et al. |
| D457,955 S | 5/2002 | Bilitz |
| 6,406,442 B1 | 6/2002 | McFann et al. |
| D460,179 S | 7/2002 | Isoda et al. |
| 6,422,989 B1 | 7/2002 | Hektner |
| 6,436,070 B1 | 8/2002 | Botich et al. |
| 6,436,112 B2 | 8/2002 | Wensel et al. |
| 6,443,929 B1 | 9/2002 | Kuracina et al. |
| 6,451,052 B1 | 9/2002 | Burmeister et al. |
| 6,461,362 B1 | 10/2002 | Halseth et al. |
| 6,475,217 B1 | 11/2002 | Platt |
| 6,478,779 B1 | 11/2002 | Hu |
| 6,485,473 B1 | 11/2002 | Lynn |
| 6,485,497 B2 | 11/2002 | Wensel et al. |
| 6,497,681 B1 | 12/2002 | Brenner |
| 6,506,181 B2 | 1/2003 | Meng et al. |
| 6,514,236 B1 | 2/2003 | Stratienko |
| 6,524,276 B1 | 2/2003 | Halseth et al. |
| D471,980 S | 3/2003 | Caizza |
| 6,527,759 B1 | 3/2003 | Tachibana et al. |
| 6,530,913 B1 | 3/2003 | Giba et al. |
| 6,530,935 B2 | 3/2003 | Wensel et al. |
| 6,540,725 B1 | 4/2003 | Ponzi |
| 6,540,732 B1 | 4/2003 | Botich et al. |
| 6,544,239 B2 | 4/2003 | Kinsey et al. |
| 6,547,762 B1 * | 4/2003 | Botich ............ A61M 25/09041 604/110 |
| 6,558,355 B1 | 5/2003 | Metzger et al. |
| 6,582,402 B1 | 6/2003 | Erskine |
| 6,582,440 B1 | 6/2003 | Brumbach |
| 6,585,703 B1 | 7/2003 | Kassel et al. |

(56) References Cited

U.S. PATENT DOCUMENTS

| | | |
|---|---|---|
| 6,589,262 B1 | 7/2003 | Honebrink et al. |
| 6,595,955 B2 | 7/2003 | Ferguson et al. |
| 6,595,959 B1 | 7/2003 | Stratienko |
| 6,599,296 B1 | 7/2003 | Gillick et al. |
| 6,607,511 B2 | 8/2003 | Halseth et al. |
| 6,616,630 B1 | 9/2003 | Woehr et al. |
| 6,620,136 B1 | 9/2003 | Pressly, Sr. et al. |
| 6,623,449 B2 | 9/2003 | Paskar |
| 6,623,456 B1 | 9/2003 | Holdaway et al. |
| 6,626,868 B1 | 9/2003 | Prestidge et al. |
| 6,626,869 B1 | 9/2003 | Bint |
| 6,629,959 B2 | 10/2003 | Kuracina et al. |
| 6,632,201 B1 | 10/2003 | Mathias et al. |
| 6,638,252 B2 | 10/2003 | Moulton et al. |
| 6,641,564 B1 | 11/2003 | Kraus |
| 6,645,178 B1 | 11/2003 | Junker et al. |
| 6,652,486 B2 | 11/2003 | Bialecki et al. |
| 6,652,490 B2 | 11/2003 | Howell |
| 6,663,577 B2 | 12/2003 | Jen et al. |
| 6,663,592 B2 | 12/2003 | Rhad et al. |
| 6,666,865 B2 | 12/2003 | Platt |
| 6,679,900 B2 | 1/2004 | Kieturakis et al. |
| 6,689,102 B2 | 2/2004 | Greene |
| 6,692,508 B2 | 2/2004 | Wensel et al. |
| 6,692,509 B2 | 2/2004 | Wensel et al. |
| 6,695,814 B2 | 2/2004 | Greene et al. |
| 6,695,856 B2 | 2/2004 | Kieturakis et al. |
| 6,695,860 B1 | 2/2004 | Ward et al. |
| 6,699,221 B2 | 3/2004 | Vaillancourt |
| 6,702,811 B2 | 3/2004 | Stewart et al. |
| 6,706,018 B2 | 3/2004 | Westlund et al. |
| 6,711,444 B2 | 3/2004 | Koblish |
| 6,712,790 B1 | 3/2004 | Prestidge et al. |
| 6,712,797 B1 | 3/2004 | Southern, Jr. |
| 6,716,197 B2 | 4/2004 | Svendsen |
| 6,730,062 B2 | 5/2004 | Hoffman et al. |
| 6,740,063 B2 | 5/2004 | Lynn |
| 6,740,096 B2 | 5/2004 | Teague et al. |
| 6,745,080 B2 | 6/2004 | Koblish |
| 6,749,588 B1 | 6/2004 | Howell et al. |
| 6,764,468 B1 | 7/2004 | East |
| D494,270 S | 8/2004 | Reschke |
| 6,776,788 B1 | 8/2004 | Klint et al. |
| 6,796,962 B2 | 9/2004 | Ferguson et al. |
| 6,824,545 B2 | 11/2004 | Sepetka et al. |
| 6,832,715 B2 | 12/2004 | Eungard et al. |
| 6,835,190 B2 | 12/2004 | Nguyen |
| 6,837,867 B2 | 1/2005 | Kortelling |
| 6,860,871 B2 | 3/2005 | Kuracina et al. |
| 6,872,193 B2 | 3/2005 | Shaw et al. |
| 6,887,220 B2 | 5/2005 | Hogendijk |
| 6,902,546 B2 | 6/2005 | Ferguson |
| 6,905,483 B2 | 6/2005 | Newby et al. |
| 6,913,595 B2 | 7/2005 | Mastorakis |
| 6,916,311 B2 | 7/2005 | Vojtasek |
| 6,921,386 B2 | 7/2005 | Shue et al. |
| 6,921,391 B1 | 7/2005 | Barker et al. |
| 6,929,624 B1 | 8/2005 | Del Castillo |
| 6,939,325 B2 | 9/2005 | Haining |
| 6,942,652 B1 | 9/2005 | Pressly, Sr. et al. |
| 6,953,448 B2 | 10/2005 | Moulton et al. |
| 6,958,054 B2 | 10/2005 | Fitzgerald |
| 6,958,055 B2 | 10/2005 | Donnan et al. |
| 6,960,191 B2 | 11/2005 | Howlett et al. |
| 6,972,002 B2 | 12/2005 | Thorne |
| 6,974,438 B2 | 12/2005 | Shekalim |
| 6,994,693 B2 | 2/2006 | Tal |
| 7,001,396 B2 | 2/2006 | Glazier et al. |
| 7,004,927 B2 | 2/2006 | Ferguson et al. |
| 7,008,404 B2 | 3/2006 | Nakajima |
| 7,018,372 B2 | 3/2006 | Casey et al. |
| 7,018,390 B2 | 3/2006 | Turovskiy et al. |
| 7,025,746 B2 | 4/2006 | Tal |
| 7,029,467 B2 | 4/2006 | Currier et al. |
| 7,033,335 B2 | 4/2006 | Haarala et al. |
| 7,044,935 B2 | 5/2006 | Shue et al. |
| 7,060,055 B2 | 6/2006 | Wilkinson et al. |
| 7,090,656 B1 | 8/2006 | Botich et al. |
| 7,094,243 B2 | 8/2006 | Mulholland et al. |
| 7,097,633 B2 | 8/2006 | Botich et al. |
| 7,125,396 B2 | 10/2006 | Leinsing et al. |
| 7,125,397 B2 | 10/2006 | Woehr et al. |
| 7,141,040 B2 | 11/2006 | Lichtenberg |
| 7,153,276 B2 | 12/2006 | Barker et al. |
| 7,163,520 B2 | 1/2007 | Bernard et al. |
| 7,169,159 B2 | 1/2007 | Green et al. |
| 7,179,244 B2 | 2/2007 | Smith et al. |
| 7,186,239 B2 | 3/2007 | Woehr |
| 7,191,900 B2 | 3/2007 | Opie et al. |
| 7,192,433 B2 | 3/2007 | Osypka et al. |
| 7,204,813 B2 | 4/2007 | Shue et al. |
| 7,214,211 B2 | 5/2007 | Woehr et al. |
| 7,255,685 B2 | 8/2007 | Pressly, Sr. et al. |
| 7,264,613 B2 | 9/2007 | Woehr et al. |
| 7,291,130 B2 | 11/2007 | McGurk |
| 7,303,547 B2 | 12/2007 | Pressly, Sr. et al. |
| 7,303,548 B2 | 12/2007 | Rhad et al. |
| 7,314,462 B2 | 1/2008 | O'Reagan et al. |
| 7,331,966 B2 | 2/2008 | Soma et al. |
| 7,344,516 B2 | 3/2008 | Erskine |
| 7,354,422 B2 | 4/2008 | Riesenberger et al. |
| 7,374,554 B2 | 5/2008 | Menzi et al. |
| 7,381,205 B2 | 6/2008 | Thommen |
| 7,396,346 B2 | 7/2008 | Nakajima |
| 7,413,562 B2 | 8/2008 | Ferguson et al. |
| 7,422,572 B2 | 9/2008 | Popov et al. |
| 7,458,954 B2 | 12/2008 | Ferguson et al. |
| 7,465,294 B1 | 12/2008 | Vladimirsky |
| 7,468,057 B2 | 12/2008 | Ponzi |
| 7,470,254 B2 * | 12/2008 | Basta .............. A61M 25/09041 604/167.04 |
| 7,491,176 B2 | 2/2009 | Mann |
| 7,494,010 B2 | 2/2009 | Opie et al. |
| 7,500,965 B2 | 3/2009 | Menzi et al. |
| 7,507,222 B2 | 3/2009 | Cindrich et al. |
| 7,513,887 B2 | 4/2009 | Halseth et al. |
| 7,513,888 B2 | 4/2009 | Sircom et al. |
| 7,524,306 B2 | 4/2009 | Botich et al. |
| 7,530,965 B2 | 5/2009 | Villa et al. |
| 7,534,227 B2 | 5/2009 | Kulli |
| 7,534,231 B2 | 5/2009 | Kuracina et al. |
| 7,544,170 B2 | 6/2009 | Williams et al. |
| 7,556,617 B2 | 7/2009 | Voorhees, Jr. et al. |
| 7,566,323 B2 | 7/2009 | Chang |
| D601,243 S | 9/2009 | Bierman et al. |
| 7,597,681 B2 | 10/2009 | Sutton et al. |
| 7,608,057 B2 | 10/2009 | Woehr et al. |
| D604,839 S | 11/2009 | Crawford et al. |
| 7,611,485 B2 | 11/2009 | Ferguson |
| 7,611,487 B2 | 11/2009 | Woehr et al. |
| 7,611,499 B2 | 11/2009 | Woehr et al. |
| 7,618,395 B2 | 11/2009 | Ferguson |
| 7,625,360 B2 | 12/2009 | Woehr et al. |
| 7,628,769 B2 | 12/2009 | Grandt et al. |
| 7,632,243 B2 | 12/2009 | Bialecki et al. |
| 7,645,263 B2 | 1/2010 | Angel et al. |
| 7,654,988 B2 | 2/2010 | Moulton et al. |
| 7,658,725 B2 | 2/2010 | Bialecki et al. |
| D612,043 S | 3/2010 | Young et al. |
| 7,678,080 B2 | 3/2010 | Shue et al. |
| 7,682,358 B2 | 3/2010 | Gullickson et al. |
| 7,691,088 B2 | 4/2010 | Howell |
| 7,691,090 B2 | 4/2010 | Belley et al. |
| 7,691,093 B2 | 4/2010 | Brimhall |
| 7,695,458 B2 | 4/2010 | Belley et al. |
| 7,699,807 B2 | 4/2010 | Faust et al. |
| D615,197 S | 5/2010 | Koh et al. |
| 7,708,721 B2 | 5/2010 | Khaw |
| 7,713,243 B2 | 5/2010 | Hillman |
| 7,717,875 B2 | 5/2010 | Knudson et al. |
| 7,722,567 B2 | 5/2010 | Tal |
| 7,722,569 B2 | 5/2010 | Soderholm et al. |
| D617,893 S | 6/2010 | Bierman et al. |
| 7,731,687 B2 | 6/2010 | Menzi et al. |

(56) References Cited

U.S. PATENT DOCUMENTS

| | | | |
|---|---|---|---|
| 7,731,691 B2 | 6/2010 | Cote et al. |
| 7,736,332 B2 | 6/2010 | Carlyon et al. |
| 7,736,337 B2 | 6/2010 | Diep et al. |
| 7,736,339 B2 | 6/2010 | Woehr et al. |
| 7,736,342 B2 | 6/2010 | Abriles et al. |
| 7,740,615 B2 | 6/2010 | Shaw et al. |
| 7,744,574 B2 | 6/2010 | Pederson et al. |
| 7,753,877 B2 | 7/2010 | Bialecki et al. |
| 7,753,887 B2 | 7/2010 | Botich et al. |
| 7,762,984 B2 | 7/2010 | Kumoyama et al. |
| 7,762,993 B2 | 7/2010 | Perez |
| 7,766,879 B2 | 8/2010 | Tan et al. |
| 7,776,052 B2 | 8/2010 | Greenberg et al. |
| 7,785,296 B2 | 8/2010 | Muskatello et al. |
| 7,794,424 B2 | 9/2010 | Paskar |
| 7,798,994 B2 | 9/2010 | Brimhall |
| 7,803,142 B2 | 9/2010 | Longson et al. |
| 7,828,773 B2 | 11/2010 | Swisher et al. |
| 7,828,774 B2 | 11/2010 | Harding et al. |
| 7,833,201 B2 | 11/2010 | Carlyon et al. |
| 7,850,644 B2 | 12/2010 | Gonzalez et al. |
| 7,857,770 B2 | 12/2010 | Raulerson et al. |
| D634,843 S | 3/2011 | Kim et al. |
| 7,896,862 B2 | 3/2011 | Long et al. |
| 7,905,857 B2 | 3/2011 | Swisher |
| 7,914,488 B2 | 3/2011 | Dickerson |
| 7,914,492 B2 | 3/2011 | Heuser |
| 7,922,696 B2 | 4/2011 | Tal et al. |
| 7,922,698 B2 | 4/2011 | Riesenberger et al. |
| 7,927,314 B2 | 4/2011 | Kuracina et al. |
| 7,935,080 B2 | 5/2011 | Howell et al. |
| 7,959,613 B2 | 6/2011 | Rhad et al. |
| 7,972,313 B2 | 7/2011 | Woehr et al. |
| 7,972,324 B2 | 7/2011 | Quint |
| D643,531 S | 8/2011 | van der Weiden |
| 8,029,470 B2 | 10/2011 | Whiting et al. |
| 8,029,472 B2 | 10/2011 | Leinsing et al. |
| 8,048,031 B2 | 11/2011 | Shaw et al. |
| 8,048,039 B2 | 11/2011 | Carlyon et al. |
| 8,057,404 B2 | 11/2011 | Fujiwara et al. |
| 8,062,261 B2 | 11/2011 | Adams |
| 8,075,529 B2 | 12/2011 | Nakajima et al. |
| 8,079,979 B2 | 12/2011 | Moorehead |
| D653,329 S | 1/2012 | Lee-Sepsick |
| 8,100,858 B2 | 1/2012 | Woehr et al. |
| 8,105,286 B2 | 1/2012 | Anderson et al. |
| 8,105,315 B2 | 1/2012 | Johnson et al. |
| 8,123,727 B2 | 2/2012 | Luther et al. |
| 8,152,758 B2 | 4/2012 | Chan et al. |
| 8,162,881 B2 | 4/2012 | Lilley, Jr. et al. |
| 8,167,851 B2 | 5/2012 | Sen |
| 8,177,753 B2 | 5/2012 | Vitullo et al. |
| RE43,473 E | 6/2012 | Newby et al. |
| 8,192,402 B2 | 6/2012 | Anderson et al. |
| 8,202,251 B2 | 6/2012 | Bierman et al. |
| 8,202,253 B1 | 6/2012 | Wexler |
| 8,206,343 B2 | 6/2012 | Racz |
| 8,211,070 B2 | 7/2012 | Woehr et al. |
| 8,221,387 B2 | 7/2012 | Shelso et al. |
| 8,226,612 B2 | 7/2012 | Nakajima |
| 8,235,945 B2 | 8/2012 | Baid |
| 8,251,923 B2 | 8/2012 | Carrez et al. |
| 8,251,950 B2 | 8/2012 | Albert et al. |
| D667,111 S | 9/2012 | Robinson |
| 8,257,322 B2 | 9/2012 | Koehler et al. |
| 8,273,054 B2 | 9/2012 | St. Germain et al. |
| 8,286,657 B2 | 10/2012 | Belley et al. |
| 8,298,186 B2 | 10/2012 | Popov |
| 8,303,543 B2 | 11/2012 | Abulhaj |
| 8,308,685 B2 | 11/2012 | Botich et al. |
| 8,308,691 B2 | 11/2012 | Woehr et al. |
| D672,456 S | 12/2012 | Lee-Sepsick |
| 8,323,249 B2 | 12/2012 | White et al. |
| 8,328,762 B2 | 12/2012 | Woehr et al. |
| 8,328,837 B2 | 12/2012 | Binmoeller |
| 8,333,735 B2 | 12/2012 | Woehr et al. |
| 8,337,424 B2 | 12/2012 | Palmer et al. |
| 8,337,463 B2 | 12/2012 | Woehr et al. |
| 8,337,471 B2 | 12/2012 | Baid |
| D675,318 S | 1/2013 | Luk et al. |
| 8,361,020 B2 | 1/2013 | Stout |
| 8,361,038 B2 | 1/2013 | McKinnon et al. |
| 8,376,994 B2 | 2/2013 | Woehr et al. |
| 8,377,006 B2 | 2/2013 | Tal et al. |
| 8,382,721 B2 | 2/2013 | Woehr et al. |
| 8,388,583 B2 | 3/2013 | Stout et al. |
| 8,403,886 B2 | 3/2013 | Bialecki et al. |
| 8,412,300 B2 | 4/2013 | Sonderegger |
| 8,414,539 B1 | 4/2013 | Kuracina et al. |
| 8,419,688 B2 | 4/2013 | Woehr et al. |
| 8,444,605 B2 | 5/2013 | Kuracina et al. |
| 8,454,536 B2 | 6/2013 | Raulerson et al. |
| 8,460,247 B2 | 6/2013 | Woehr et al. |
| 8,469,928 B2 | 6/2013 | Stout et al. |
| 8,496,628 B2 | 7/2013 | Erskine |
| D687,548 S | 8/2013 | Hayashi |
| 8,506,533 B2 | 8/2013 | Carlyon et al. |
| 8,509,340 B2 | 8/2013 | Michelitsch |
| 8,517,959 B2 | 8/2013 | Kurosawa et al. |
| 8,529,515 B2 | 9/2013 | Woehr et al. |
| 8,535,271 B2 | 9/2013 | Fuchs et al. |
| 8,540,728 B2 | 9/2013 | Woehr et al. |
| 8,545,454 B2 | 10/2013 | Kuracina et al. |
| 8,568,372 B2 | 10/2013 | Woehr et al. |
| 8,574,203 B2 | 11/2013 | Stout et al. |
| 8,579,881 B2 | 11/2013 | Agro et al. |
| 8,585,651 B2 | 11/2013 | Asai |
| 8,585,660 B2 | 11/2013 | Murphy |
| 8,591,467 B2 | 11/2013 | Walker et al. |
| 8,591,468 B2 | 11/2013 | Woehr et al. |
| 8,597,249 B2 | 12/2013 | Woehr et al. |
| 8,622,931 B2 | 1/2014 | Teague et al. |
| 8,622,958 B2 | 1/2014 | Jones et al. |
| 8,622,972 B2 | 1/2014 | Nystrom et al. |
| D700,318 S | 2/2014 | Amoah et al. |
| 8,647,301 B2 | 2/2014 | Bialecki et al. |
| 8,647,313 B2 | 2/2014 | Woehr et al. |
| 8,647,324 B2 | 2/2014 | DeLegge et al. |
| 8,652,104 B2 | 2/2014 | Goral et al. |
| 8,657,790 B2 | 2/2014 | Tal et al. |
| 8,672,888 B2 | 3/2014 | Tal |
| 8,679,063 B2 * | 3/2014 | Stout ............... A61M 25/0097 |
| | | 604/167.04 |
| 8,690,833 B2 | 4/2014 | Belson |
| 8,715,242 B2 | 5/2014 | Helm, Jr. |
| 8,721,546 B2 | 5/2014 | Belson |
| 8,728,030 B2 | 5/2014 | Woehr |
| 8,728,035 B2 | 5/2014 | Warring et al. |
| 8,740,859 B2 | 6/2014 | McKinnon et al. |
| 8,740,964 B2 | 6/2014 | Hartley |
| 8,747,387 B2 | 6/2014 | Belley et al. |
| 8,753,317 B2 | 6/2014 | Osborne et al. |
| 8,764,711 B2 | 7/2014 | Kuracina et al. |
| D710,495 S | 8/2014 | Wu et al. |
| 8,814,833 B2 | 8/2014 | Farrell et al. |
| D713,957 S | 9/2014 | Woehr et al. |
| D714,436 S | 9/2014 | Lee-Sepsick |
| 8,827,965 B2 | 9/2014 | Woehr et al. |
| 8,845,584 B2 | 9/2014 | Ferguson et al. |
| D715,931 S | 10/2014 | Watanabe et al. |
| 8,864,714 B2 | 10/2014 | Harding et al. |
| 8,900,192 B2 | 12/2014 | Anderson et al. |
| 8,932,257 B2 | 1/2015 | Woehr |
| 8,932,258 B2 | 1/2015 | Blanchard et al. |
| 8,932,259 B2 | 1/2015 | Stout et al. |
| 8,945,011 B2 | 2/2015 | Sheldon et al. |
| 8,951,230 B2 * | 2/2015 | Tanabe ............... A61M 5/158 |
| | | 604/167.03 |
| 8,956,327 B2 | 2/2015 | Bierman et al. |
| 8,974,426 B2 | 3/2015 | Corcoran et al. |
| 8,979,802 B2 | 3/2015 | Woehr |
| 8,986,227 B2 | 3/2015 | Belson |
| D726,908 S | 4/2015 | Yu et al. |
| 8,998,852 B2 | 4/2015 | Blanchard et al. |

(56) References Cited

U.S. PATENT DOCUMENTS

| | | |
|---|---|---|
| 9,005,169 B2 | 4/2015 | Gravesen et al. |
| 9,011,351 B2 | 4/2015 | Hoshinouchi |
| 9,011,381 B2 | 4/2015 | Yamada et al. |
| D728,781 S | 5/2015 | Pierson et al. |
| 9,022,979 B2 | 5/2015 | Woehr |
| 9,033,927 B2 | 5/2015 | Maan et al. |
| D733,289 S | 6/2015 | Blanchard et al. |
| 9,044,583 B2 | 6/2015 | Vaillancourt |
| D735,321 S | 7/2015 | Blanchard |
| 9,089,671 B2 | 7/2015 | Stout et al. |
| 9,089,674 B2 | 7/2015 | Ginn et al. |
| 9,095,683 B2 | 8/2015 | Hall et al. |
| 9,101,746 B2 | 8/2015 | Stout et al. |
| 9,108,021 B2 | 8/2015 | Hyer et al. |
| 9,114,231 B2 | 8/2015 | Woehr et al. |
| 9,114,241 B2 | 8/2015 | Stout et al. |
| 9,126,012 B2 | 9/2015 | McKinnon et al. |
| 9,138,252 B2 | 9/2015 | Bierman et al. |
| 9,138,545 B2 | 9/2015 | Shaw et al. |
| 9,138,559 B2 | 9/2015 | Odland et al. |
| RE45,776 E | 10/2015 | Root et al. |
| D740,410 S | 10/2015 | Korkuch et al. |
| 9,149,625 B2 | 10/2015 | Woehr et al. |
| 9,149,626 B2 | 10/2015 | Woehr et al. |
| 9,155,863 B2 | 10/2015 | Isaacson et al. |
| 9,162,036 B2 | 10/2015 | Caples et al. |
| 9,162,037 B2 | 10/2015 | Belson et al. |
| 9,180,275 B2 | 11/2015 | Helm |
| D746,445 S | 12/2015 | Lazarus |
| 9,205,231 B2 | 12/2015 | Call et al. |
| 9,216,109 B2 | 12/2015 | Badawi et al. |
| 9,220,531 B2 | 12/2015 | Datta et al. |
| 9,220,871 B2 | 12/2015 | Thorne et al. |
| 9,220,882 B2 | 12/2015 | Belley et al. |
| D748,254 S | 1/2016 | Freigang et al. |
| 9,227,038 B2 | 1/2016 | Woehr |
| 9,242,071 B2 | 1/2016 | Morgan et al. |
| 9,242,072 B2 | 1/2016 | Morgan et al. |
| RE45,896 E | 2/2016 | Stout et al. |
| D748,774 S | 2/2016 | Caron |
| D748,777 S | 2/2016 | Uenishi et al. |
| D749,214 S | 2/2016 | Uenishi et al. |
| D749,727 S | 2/2016 | Wapler et al. |
| D751,194 S | 3/2016 | Yu et al. |
| D752,737 S | 3/2016 | Ohashi |
| 9,289,237 B2 | 3/2016 | Woehr et al. |
| 9,308,352 B2 | 4/2016 | Teoh et al. |
| 9,308,354 B2 | 4/2016 | Farrell et al. |
| 9,320,870 B2 | 4/2016 | Woehr |
| D755,368 S | 5/2016 | Efinger et al. |
| 9,352,119 B2 | 5/2016 | Burkholz et al. |
| 9,352,127 B2 | 5/2016 | Yeh et al. |
| 9,352,129 B2 | 5/2016 | Nardeo et al. |
| 9,358,364 B2 * | 6/2016 | Isaacson ............ A61B 5/15003 |
| 9,370,641 B2 | 6/2016 | Woehr et al. |
| 9,381,324 B2 | 7/2016 | Fuchs et al. |
| 9,399,116 B2 | 7/2016 | Goral et al. |
| 9,408,569 B2 | 8/2016 | Andreae et al. |
| 9,421,345 B2 | 8/2016 | Woehr et al. |
| 9,427,549 B2 | 8/2016 | Woehr et al. |
| D775,330 S | 12/2016 | Blennow et al. |
| 9,522,254 B2 | 12/2016 | Belson |
| D776,259 S | 1/2017 | Eldredge |
| 9,545,495 B2 | 1/2017 | Goral et al. |
| 9,554,817 B2 | 1/2017 | Goldfarb et al. |
| D779,059 S | 2/2017 | Nino et al. |
| D779,661 S | 2/2017 | McKnight et al. |
| 9,579,486 B2 | 2/2017 | Burkholz et al. |
| 9,586,027 B2 | 3/2017 | Tisci et al. |
| 9,592,367 B2 | 3/2017 | Harding et al. |
| 9,616,201 B2 | 4/2017 | Belson |
| 9,623,210 B2 | 4/2017 | Woehr |
| 9,675,784 B2 | 6/2017 | Belson |
| 9,687,633 B2 | 6/2017 | Teoh |
| D791,311 S | 7/2017 | Yantz |
| 9,707,378 B2 | 7/2017 | Leinsing et al. |
| 9,717,523 B2 | 8/2017 | Feng et al. |
| 9,717,887 B2 | 8/2017 | Tan |
| 9,737,252 B2 | 8/2017 | Teoh et al. |
| 9,750,532 B2 | 9/2017 | Toomey et al. |
| 9,750,928 B2 | 9/2017 | Burkholz et al. |
| 9,757,540 B2 | 9/2017 | Belson |
| 9,764,085 B2 | 9/2017 | Teoh |
| 9,764,117 B2 | 9/2017 | Bierman et al. |
| 9,775,972 B2 | 10/2017 | Christensen et al. |
| 9,782,568 B2 | 10/2017 | Belson |
| 9,789,279 B2 | 10/2017 | Burkholz et al. |
| 9,795,766 B2 | 10/2017 | Teoh |
| 9,844,646 B2 | 12/2017 | Knutsson |
| 9,861,792 B2 | 1/2018 | Hall et al. |
| 9,872,971 B2 | 1/2018 | Blanchard |
| D810,282 S | 2/2018 | Ratjen |
| D815,737 S | 4/2018 | Bergstrom et al. |
| 9,950,139 B2 | 4/2018 | Blanchard et al. |
| 9,962,525 B2 | 5/2018 | Woehr |
| 10,004,878 B2 | 6/2018 | Ishida |
| 10,086,171 B2 | 10/2018 | Belson |
| 10,232,146 B2 | 3/2019 | Braithwaite et al. |
| 10,328,239 B2 | 6/2019 | Belson |
| 10,357,635 B2 | 7/2019 | Korkuch et al. |
| 10,384,039 B2 | 8/2019 | Ribelin et al. |
| 10,426,931 B2 | 10/2019 | Blanchard et al. |
| D870,271 S | 12/2019 | Kheradpir et al. |
| D870,883 S | 12/2019 | Harding et al. |
| 10,493,262 B2 | 12/2019 | Tran et al. |
| 10,525,236 B2 | 1/2020 | Belson |
| 10,688,280 B2 | 6/2020 | Blanchard et al. |
| 10,688,281 B2 | 6/2020 | Blanchard et al. |
| 10,722,685 B2 | 7/2020 | Blanchard et al. |
| 10,806,906 B2 | 10/2020 | Warring et al. |
| 11,389,626 B2 | 7/2022 | Tran et al. |
| 11,400,260 B2 | 8/2022 | Huang et al. |
| 2001/0014786 A1 | 8/2001 | Greene et al. |
| 2001/0020153 A1 | 9/2001 | Howell |
| 2002/0052576 A1 | 5/2002 | Massengale |
| 2002/0077595 A1 | 6/2002 | Hundertmark et al. |
| 2002/0103446 A1 | 8/2002 | McFann et al. |
| 2002/0107526 A1 | 8/2002 | Greenberg et al. |
| 2002/0128604 A1 * | 9/2002 | Nakajima ......... A61M 39/0693 604/167.04 |
| 2002/0165497 A1 | 11/2002 | Greene |
| 2002/0177812 A1 | 11/2002 | Moulton et al. |
| 2003/0032922 A1 | 2/2003 | Moorehead |
| 2003/0032936 A1 | 2/2003 | Lederman |
| 2003/0060760 A1 | 3/2003 | Botich et al. |
| 2003/0073956 A1 | 4/2003 | Hoffman et al. |
| 2003/0120214 A1 | 6/2003 | Howell |
| 2003/0153874 A1 | 8/2003 | Tal |
| 2003/0187396 A1 | 10/2003 | Ponzi |
| 2003/0204186 A1 | 10/2003 | Geistert |
| 2004/0019329 A1 | 1/2004 | Erskine |
| 2004/0030291 A1 * | 2/2004 | Holdaway ......... A61M 25/0643 604/164.08 |
| 2004/0034383 A1 | 2/2004 | Belson |
| 2004/0044302 A1 | 3/2004 | Bernard et al. |
| 2004/0044313 A1 | 3/2004 | Nakajima |
| 2004/0092879 A1 | 5/2004 | Kraus et al. |
| 2004/0106903 A1 | 6/2004 | Shue et al. |
| 2004/0111059 A1 | 6/2004 | Howlett et al. |
| 2004/0122373 A1 | 6/2004 | Botich et al. |
| 2004/0176758 A1 | 9/2004 | Yassinzadeh |
| 2004/0193118 A1 | 9/2004 | Bergeron |
| 2004/0215146 A1 * | 10/2004 | Lampropoulos ... A61B 5/15003 604/168.01 |
| 2004/0236288 A1 * | 11/2004 | Howell ............ A61M 25/0618 604/263 |
| 2004/0243061 A1 | 12/2004 | McGurk |
| 2004/0267204 A1 | 12/2004 | Brustowicz |
| 2005/0004524 A1 | 1/2005 | Newby et al. |
| 2005/0004532 A1 | 1/2005 | Woehr et al. |
| 2005/0010095 A1 | 1/2005 | Stewart et al. |
| 2005/0020940 A1 | 1/2005 | Opie et al. |
| 2005/0021002 A1 | 1/2005 | Deckman et al. |

(56) References Cited

U.S. PATENT DOCUMENTS

| | | |
|---|---|---|
| 2005/0027256 A1* | 2/2005 | Barker .............. A61B 5/150389 604/164.12 |
| 2005/0033137 A1 | 2/2005 | Oral et al. |
| 2005/0040061 A1 | 2/2005 | Opie et al. |
| 2005/0075606 A1 | 4/2005 | Botich et al. |
| 2005/0107769 A1 | 5/2005 | Thommen |
| 2005/0119619 A1 | 6/2005 | Haining |
| 2005/0131350 A1 | 6/2005 | Shaw et al. |
| 2005/0165355 A1 | 7/2005 | Fitzgerald |
| 2005/0197623 A1 | 9/2005 | Leeflang et al. |
| 2005/0245847 A1 | 11/2005 | Schaeffer |
| 2005/0256505 A1 | 11/2005 | Long et al. |
| 2005/0273057 A1 | 12/2005 | Popov |
| 2006/0025721 A1 | 2/2006 | Duffy et al. |
| 2006/0036219 A1 | 2/2006 | Alvin |
| 2006/0079787 A1 | 4/2006 | Whiting et al. |
| 2006/0084964 A1 | 4/2006 | Knudson et al. |
| 2006/0155245 A1* | 7/2006 | Woehr .............. A61M 39/0693 604/110 |
| 2006/0161115 A1 | 7/2006 | Fangrow |
| 2006/0167405 A1 | 7/2006 | King et al. |
| 2006/0200080 A1* | 9/2006 | Abulhaj ............ A61M 25/0631 604/164.01 |
| 2006/0229563 A1 | 10/2006 | O'Reagan et al. |
| 2006/0264834 A1 | 11/2006 | Vaillancourt |
| 2006/0264841 A1* | 11/2006 | Cote .................... A61M 39/26 604/247 |
| 2007/0043422 A1 | 2/2007 | Shmulewitz et al. |
| 2007/0060999 A1 | 3/2007 | Randall et al. |
| 2007/0083162 A1 | 4/2007 | O'Reagan et al. |
| 2007/0083188 A1 | 4/2007 | Grandt et al. |
| 2007/0100284 A1 | 5/2007 | Leinsing et al. |
| 2007/0123803 A1 | 5/2007 | Fujiwara et al. |
| 2007/0142779 A1 | 6/2007 | Duane et al. |
| 2007/0179446 A1 | 8/2007 | Carrez et al. |
| 2007/0191777 A1 | 8/2007 | King |
| 2007/0191786 A1* | 8/2007 | Raines .................. A61M 39/26 264/407 |
| 2007/0193903 A1 | 8/2007 | Opie et al. |
| 2007/0225647 A1 | 9/2007 | Luther et al. |
| 2007/0233007 A1* | 10/2007 | Adams .............. A61M 25/0097 604/168.01 |
| 2007/0244438 A1* | 10/2007 | Perez ................ A61M 25/0631 604/164.01 |
| 2007/0255221 A1 | 11/2007 | Nakajima |
| 2007/0276288 A1 | 11/2007 | Khaw |
| 2008/0039796 A1 | 2/2008 | Nakajima |
| 2008/0065011 A1 | 3/2008 | Marchand et al. |
| 2008/0082082 A1 | 4/2008 | Carlyon et al. |
| 2008/0097330 A1 | 4/2008 | King et al. |
| 2008/0108911 A1 | 5/2008 | Palmer et al. |
| 2008/0108944 A1* | 5/2008 | Woehr .............. A61M 39/0693 604/164.08 |
| 2008/0108974 A1 | 5/2008 | Yee Roth |
| 2008/0125709 A1 | 5/2008 | Chang et al. |
| 2008/0131300 A1 | 6/2008 | Junod et al. |
| 2008/0132846 A1 | 6/2008 | Shue et al. |
| 2008/0147010 A1 | 6/2008 | Nakajima et al. |
| 2008/0243165 A1 | 10/2008 | Mauch et al. |
| 2008/0262430 A1 | 10/2008 | Anderson et al. |
| 2008/0262431 A1 | 10/2008 | Anderson et al. |
| 2008/0294111 A1 | 11/2008 | Tal et al. |
| 2008/0300574 A1 | 12/2008 | Belson et al. |
| 2009/0018567 A1* | 1/2009 | Escudero ........ A61B 17/320758 606/159 |
| 2009/0030380 A1 | 1/2009 | Binmoeller |
| 2009/0036836 A1 | 2/2009 | Nystrom et al. |
| 2009/0048566 A1 | 2/2009 | Ferguson et al. |
| 2009/0131872 A1 | 5/2009 | Popov |
| 2009/0157006 A1 | 6/2009 | Nardeo et al. |
| 2009/0221961 A1 | 9/2009 | Tal et al. |
| 2009/0227953 A1 | 9/2009 | Tan et al. |
| 2009/0287154 A1* | 11/2009 | Harding ............ A61M 39/0606 604/167.04 |
| 2009/0292243 A1 | 11/2009 | Harding et al. |
| 2009/0299291 A1 | 12/2009 | Baid |
| 2010/0010441 A1 | 1/2010 | Belson |
| 2010/0010447 A1 | 1/2010 | Luther et al. |
| 2010/0016838 A1 | 1/2010 | Butts et al. |
| 2010/0036331 A1 | 2/2010 | Sen |
| 2010/0056910 A1 | 3/2010 | Yanuma |
| 2010/0057183 A1 | 3/2010 | Mangiardi et al. |
| 2010/0087787 A1 | 4/2010 | Woehr et al. |
| 2010/0094116 A1 | 4/2010 | Silverstein |
| 2010/0094310 A1 | 4/2010 | Warring et al. |
| 2010/0137815 A1 | 6/2010 | Kuracina et al. |
| 2010/0168674 A1 | 7/2010 | Shaw et al. |
| 2010/0204654 A1 | 8/2010 | Mulholland et al. |
| 2010/0204660 A1* | 8/2010 | McKinnon ........ A61M 25/0043 604/244 |
| 2010/0204675 A1 | 8/2010 | Woehr et al. |
| 2010/0210934 A1 | 8/2010 | Belson |
| 2010/0238705 A1 | 9/2010 | Kim et al. |
| 2010/0246707 A1 | 9/2010 | Michelitsch |
| 2010/0331732 A1 | 12/2010 | Raulerson et al. |
| 2011/0004162 A1 | 1/2011 | Tal |
| 2011/0009827 A1 | 1/2011 | Bierman et al. |
| 2011/0015573 A1 | 1/2011 | Maan et al. |
| 2011/0021994 A1 | 1/2011 | Anderson et al. |
| 2011/0046570 A1* | 2/2011 | Stout ................ A61M 39/0693 604/246 |
| 2011/0125097 A1 | 5/2011 | Shaw et al. |
| 2011/0137252 A1 | 6/2011 | Oster et al. |
| 2011/0196315 A1 | 8/2011 | Chappel |
| 2011/0207157 A1 | 8/2011 | Gautier et al. |
| 2011/0218496 A1 | 9/2011 | Bierman |
| 2011/0251559 A1 | 10/2011 | Tal et al. |
| 2011/0276002 A1 | 11/2011 | Bierman |
| 2011/0282285 A1 | 11/2011 | Blanchard et al. |
| 2011/0288482 A1 | 11/2011 | Farrell et al. |
| 2011/0306933 A1 | 12/2011 | Djordjevic et al. |
| 2011/0319838 A1 | 12/2011 | Goral et al. |
| 2012/0053523 A1 | 3/2012 | Harding |
| 2012/0071857 A1 | 3/2012 | Goldfarb et al. |
| 2012/0078231 A1 | 3/2012 | Hoshinouchi |
| 2012/0101440 A1 | 4/2012 | Kamen et al. |
| 2012/0123332 A1 | 5/2012 | Erskine |
| 2012/0123354 A1 | 5/2012 | Woehr |
| 2012/0157854 A1 | 6/2012 | Kumis et al. |
| 2012/0179104 A1 | 7/2012 | Woehr et al. |
| 2012/0184896 A1 | 7/2012 | DeLegge et al. |
| 2012/0197200 A1 | 8/2012 | Belson |
| 2012/0220942 A1 | 8/2012 | Hall et al. |
| 2012/0220956 A1 | 8/2012 | Kuracina et al. |
| 2012/0259293 A1 | 10/2012 | Bialecki et al. |
| 2012/0271232 A1 | 10/2012 | Katsurada et al. |
| 2012/0296282 A1 | 11/2012 | Koehler et al. |
| 2012/0310179 A1* | 12/2012 | Truitt .................... A61M 39/26 604/249 |
| 2012/0316500 A1 | 12/2012 | Bierman et al. |
| 2012/0323181 A1 | 12/2012 | Shaw et al. |
| 2013/0030391 A1 | 1/2013 | Baid |
| 2013/0158506 A1 | 6/2013 | Harris et al. |
| 2013/0184645 A1 | 7/2013 | Baid |
| 2013/0204206 A1 | 8/2013 | Morgan et al. |
| 2013/0204226 A1 | 8/2013 | Keyser |
| 2013/0218082 A1 | 8/2013 | Hyer et al. |
| 2013/0304030 A1 | 11/2013 | Gray et al. |
| 2013/0310764 A1* | 11/2013 | Burkholz .......... A61M 25/0045 604/246 |
| 2013/0324930 A1 | 12/2013 | Fuchs et al. |
| 2014/0012203 A1 | 1/2014 | Woehr et al. |
| 2014/0031752 A1 | 1/2014 | Blanchard et al. |
| 2014/0039461 A1 | 2/2014 | Anderson et al. |
| 2014/0058329 A1 | 2/2014 | Walker et al. |
| 2014/0058336 A1 | 2/2014 | Burkholz et al. |
| 2014/0058357 A1 | 2/2014 | Keyser et al. |
| 2014/0073928 A1 | 3/2014 | Yamashita et al. |
| 2014/0074034 A1 | 3/2014 | Tanabe et al. |
| 2014/0088509 A1 | 3/2014 | Sonderegger et al. |
| 2014/0094774 A1 | 4/2014 | Blanchard |
| 2014/0094836 A1 | 4/2014 | Feng et al. |
| 2014/0114239 A1 | 4/2014 | Dib et al. |

(56) References Cited

U.S. PATENT DOCUMENTS

| | | |
|---|---|---|
| 2014/0128775 A1 | 5/2014 | Andreae et al. |
| 2014/0135702 A1 | 5/2014 | Woehr et al. |
| 2014/0135703 A1 | 5/2014 | Yeh et al. |
| 2014/0143999 A1 | 5/2014 | Goral et al. |
| 2014/0180250 A1 | 6/2014 | Belson |
| 2014/0188003 A1 | 7/2014 | Belson |
| 2014/0194853 A1 | 7/2014 | Morgan et al. |
| 2014/0214005 A1 | 7/2014 | Belson |
| 2014/0221977 A1 | 8/2014 | Belson |
| 2014/0236099 A1* | 8/2014 | Nakagami ......... A61M 25/0097 604/256 |
| 2014/0243734 A1 | 8/2014 | Eubanks et al. |
| 2014/0249488 A1 | 9/2014 | Woehr |
| 2014/0257359 A1 | 9/2014 | Tegels et al. |
| 2014/0276224 A1 | 9/2014 | Ranganathan et al. |
| 2014/0276432 A1 | 9/2014 | Bierman et al. |
| 2014/0276434 A1 | 9/2014 | Woehr et al. |
| 2014/0303561 A1 | 10/2014 | Li |
| 2014/0323988 A1 | 10/2014 | Magnani et al. |
| 2014/0336582 A1 | 11/2014 | Tisci et al. |
| 2014/0357983 A1 | 12/2014 | Toomey et al. |
| 2014/0358123 A1 | 12/2014 | Ueda et al. |
| 2014/0364809 A1 | 12/2014 | Isaacson et al. |
| 2014/0371715 A1 | 12/2014 | Farrell et al. |
| 2014/0371720 A1 | 12/2014 | Urmey |
| 2014/0378867 A1 | 12/2014 | Belson |
| 2015/0025467 A1 | 1/2015 | Woehr |
| 2015/0038909 A1* | 2/2015 | Christensen ...... A61M 25/0097 604/164.07 |
| 2015/0038910 A1* | 2/2015 | Harding ............. A61M 39/221 604/167.02 |
| 2015/0038943 A1 | 2/2015 | Warring et al. |
| 2015/0051584 A1 | 2/2015 | Korkuch et al. |
| 2015/0080801 A1 | 3/2015 | Tanabe et al. |
| 2015/0080810 A1 | 3/2015 | Henderson et al. |
| 2015/0088095 A1 | 3/2015 | Luther et al. |
| 2015/0094659 A1 | 4/2015 | Schraga |
| 2015/0119806 A1 | 4/2015 | Blanchard et al. |
| 2015/0119852 A1 | 4/2015 | Wexler |
| 2015/0126932 A1 | 5/2015 | Knutsson |
| 2015/0151086 A1 | 6/2015 | Teoh |
| 2015/0151088 A1 | 6/2015 | Lim et al. |
| 2015/0190168 A1 | 7/2015 | Bierman et al. |
| 2015/0190570 A1* | 7/2015 | Teoh ................. A61M 39/0613 29/428 |
| 2015/0190617 A1 | 7/2015 | Anderson et al. |
| 2015/0202414 A1 | 7/2015 | Hwang |
| 2015/0202421 A1* | 7/2015 | Ma ..................... A61M 39/22 604/167.03 |
| 2015/0224267 A1 | 8/2015 | Farrell et al. |
| 2015/0231364 A1 | 8/2015 | Blanchard et al. |
| 2015/0238705 A1 | 8/2015 | Gravesen et al. |
| 2015/0290431 A1 | 10/2015 | Hall et al. |
| 2015/0306347 A1 | 10/2015 | Yagi |
| 2015/0306356 A1 | 10/2015 | Gill |
| 2015/0328434 A1 | 11/2015 | Gaur |
| 2015/0328438 A1 | 11/2015 | Baid |
| 2015/0335858 A1 | 11/2015 | Woehr et al. |
| 2015/0359473 A1 | 12/2015 | Garrett et al. |
| 2016/0008580 A1 | 1/2016 | Woehr et al. |
| 2016/0015943 A1 | 1/2016 | Belson et al. |
| 2016/0015945 A1 | 1/2016 | Warring et al. |
| 2016/0022312 A1 | 1/2016 | Tang et al. |
| 2016/0022963 A1 | 1/2016 | Belson |
| 2016/0030716 A1 | 2/2016 | Mallin et al. |
| 2016/0045715 A1 | 2/2016 | Galgano et al. |
| 2016/0089513 A1 | 3/2016 | Ishida |
| 2016/0106959 A1 | 4/2016 | Woehr |
| 2016/0114136 A1 | 4/2016 | Woehr |
| 2016/0114137 A1 | 4/2016 | Woehr et al. |
| 2016/0158503 A1 | 6/2016 | Woehr |
| 2016/0158526 A1 | 6/2016 | Woehr |
| 2016/0175563 A1 | 6/2016 | Woehr et al. |
| 2016/0184557 A1 | 6/2016 | Call et al. |
| 2016/0199575 A1 | 7/2016 | Belley et al. |
| 2016/0206852 A1 | 7/2016 | Morgan et al. |
| 2016/0206858 A1 | 7/2016 | Ishida |
| 2016/0220161 A1 | 8/2016 | Goral et al. |
| 2016/0220786 A1 | 8/2016 | Mitchell et al. |
| 2016/0256667 A1 | 9/2016 | Ribelin et al. |
| 2016/0296729 A1 | 10/2016 | Fuchs et al. |
| 2016/0310704 A1 | 10/2016 | Ng et al. |
| 2016/0331937 A1* | 11/2016 | Teoh ..................... A61M 39/06 |
| 2016/0331938 A1 | 11/2016 | Blanchard et al. |
| 2016/0354580 A1 | 12/2016 | Teoh et al. |
| 2016/0361490 A1 | 12/2016 | Phang et al. |
| 2016/0361519 A1 | 12/2016 | Teoh et al. |
| 2017/0000982 A1 | 1/2017 | Ishida |
| 2017/0035992 A1 | 2/2017 | Harding et al. |
| 2017/0043132 A1 | 2/2017 | Ishida |
| 2017/0080205 A1* | 3/2017 | Lauer ..................... A61M 1/36 |
| 2017/0087338 A1 | 3/2017 | Belson |
| 2017/0136217 A1 | 5/2017 | Riesenberger et al. |
| 2017/0203050 A1 | 7/2017 | Bauer et al. |
| 2017/0209668 A1 | 7/2017 | Belson |
| 2017/0246429 A1 | 8/2017 | Tan et al. |
| 2017/0259036 A1 | 9/2017 | Belson |
| 2017/0361071 A1 | 12/2017 | Belson |
| 2018/0028780 A1 | 2/2018 | Blanchard et al. |
| 2018/0071509 A1 | 3/2018 | Tran et al. |
| 2018/0099123 A1 | 4/2018 | Woehr |
| 2018/0126125 A1 | 5/2018 | Hall et al. |
| 2018/0133437 A1 | 5/2018 | Blanchard |
| 2018/0229003 A1 | 8/2018 | Blanchard et al. |
| 2018/0229004 A1 | 8/2018 | Blanchard et al. |
| 2019/0022358 A1 | 1/2019 | Belson |
| 2019/0192829 A1 | 6/2019 | Belson et al. |
| 2019/0201667 A1 | 7/2019 | Braithwaite et al. |
| 2019/0240459 A1 | 8/2019 | Belson |
| 2019/0275303 A1 | 9/2019 | Tran et al. |
| 2019/0307986 A1 | 10/2019 | Belson |
| 2019/0351193 A1 | 11/2019 | Hall |
| 2019/0351196 A1 | 11/2019 | Ribelin et al. |
| 2020/0001051 A1 | 1/2020 | Huang et al. |
| 2020/0261696 A1 | 8/2020 | Blanchard |
| 2020/0261703 A1 | 8/2020 | Belson et al. |
| 2020/0316347 A1 | 10/2020 | Belson |
| 2021/0052858 A1 | 2/2021 | Isaacson et al. |
| 2021/0308428 A1 | 10/2021 | Blanchard et al. |
| 2021/0402155 A1 | 12/2021 | Hall et al. |
| 2022/0362523 A1 | 11/2022 | Huang et al. |
| 2022/0379093 A1 | 12/2022 | Nielson |

FOREIGN PATENT DOCUMENTS

| | | |
|---|---|---|
| CN | 1178707 A | 4/1998 |
| CN | 1319023 A | 10/2001 |
| CN | 1523970 A | 8/2004 |
| CN | 1871043 A | 11/2006 |
| CN | 101242868 A | 8/2008 |
| CN | 101293122 A | 10/2008 |
| CN | 101417159 A | 4/2009 |
| CN | 101784300 A | 7/2010 |
| CN | 102099075 A | 6/2011 |
| CN | 102939129 A | 2/2013 |
| CN | 104689456 A | 6/2015 |
| CN | 105073174 A | 11/2015 |
| CN | 105188826 A | 12/2015 |
| CN | 105705191 A | 6/2016 |
| DE | 20210394 U1 | 9/2002 |
| EP | 0314470 A2 | 5/1989 |
| EP | 417764 A1 | 3/1991 |
| EP | 475857 A1 | 3/1992 |
| EP | 515710 A1 | 12/1992 |
| EP | 567321 A2 | 10/1993 |
| EP | 652020 A2 | 5/1995 |
| EP | 0730880 A1 | 9/1996 |
| EP | 747075 A2 | 12/1996 |
| EP | 750916 A2 | 1/1997 |
| EP | 778043 A1 | 6/1997 |
| EP | 800790 A2 | 10/1997 |
| EP | 832663 A2 | 4/1998 |
| EP | 910988 A1 | 4/1999 |

(56) References Cited

FOREIGN PATENT DOCUMENTS

| | | |
|---|---|---|
| EP | 942761 A1 | 9/1999 |
| EP | 1075850 A2 | 2/2001 |
| EP | 1378263 A2 | 1/2004 |
| EP | 1418971 A2 | 5/2004 |
| EP | 1457229 A1 | 9/2004 |
| EP | 1611916 A1 | 1/2006 |
| EP | 1907042 A2 | 4/2008 |
| EP | 1974765 A1 | 10/2008 |
| EP | 2150304 A2 | 2/2010 |
| EP | 2272432 A1 | 1/2011 |
| EP | 2347785 A1 | 7/2011 |
| EP | 2569046 A1 | 3/2013 |
| GB | 2529270 A | 2/2016 |
| JP | 2003-159334 A | 6/2003 |
| JP | 2004-130074 A | 4/2004 |
| JP | 2004-223252 A | 8/2004 |
| JP | 2005-137888 A | 6/2005 |
| JP | 2009-500129 A | 1/2009 |
| JP | 2010-088521 A | 4/2010 |
| JP | 2013-529111 A | 7/2013 |
| JP | 2018-118079 A | 8/2018 |
| JP | 6692869 B2 | 5/2020 |
| WO | 83/01575 A1 | 5/1983 |
| WO | 1983001575 A1 | 5/1983 |
| WO | 1992013584 A1 | 8/1992 |
| WO | 92/22344 A1 | 12/1992 |
| WO | 1992022344 A1 | 12/1992 |
| WO | 1994006681 A2 | 3/1994 |
| WO | 1995011710 A1 | 5/1995 |
| WO | 95/19193 A1 | 7/1995 |
| WO | 1995019193 A1 | 7/1995 |
| WO | 95/23003 A1 | 8/1995 |
| WO | 1995023003 A1 | 8/1995 |
| WO | 96/32981 A1 | 10/1996 |
| WO | 1996032981 A1 | 10/1996 |
| WO | 1996040359 A1 | 12/1996 |
| WO | 97/05912 A2 | 2/1997 |
| WO | 1997005912 A2 | 2/1997 |
| WO | 97/21458 A1 | 6/1997 |
| WO | 1997021458 A1 | 6/1997 |
| WO | 1997045151 A1 | 12/1997 |
| WO | 98/24494 A1 | 6/1998 |
| WO | 1998024494 A1 | 6/1998 |
| WO | 1998030268 A1 | 7/1998 |
| WO | 1998053875 A1 | 12/1998 |
| WO | 1999008742 A1 | 2/1999 |
| WO | 1999026682 A1 | 6/1999 |
| WO | 00/06226 A1 | 2/2000 |
| WO | 00/12160 A1 | 3/2000 |
| WO | 2000012167 A1 | 3/2000 |
| WO | 00/47256 A1 | 8/2000 |
| WO | 00/67829 A1 | 11/2000 |
| WO | 2001007103 A1 | 2/2001 |
| WO | 01/26725 A1 | 4/2001 |
| WO | 2002041932 A2 | 5/2002 |
| WO | 02/066093 A2 | 8/2002 |
| WO | 02/076526 A2 | 10/2002 |
| WO | 03/11381 A1 | 2/2003 |
| WO | 03/43686 A1 | 5/2003 |
| WO | 03/043686 A1 | 5/2003 |
| WO | 03/47675 A2 | 6/2003 |
| WO | 03/047675 A2 | 6/2003 |
| WO | 2004/018031 A2 | 3/2004 |
| WO | 2005002659 A1 | 1/2005 |
| WO | 2004106203 A3 | 3/2005 |
| WO | 2005/074412 A2 | 8/2005 |
| WO | 2005/087306 A1 | 9/2005 |
| WO | 2006062996 A2 | 6/2006 |
| WO | 2007006055 A2 | 1/2007 |
| WO | 2007/032343 A1 | 3/2007 |
| WO | 2007094841 A1 | 8/2007 |
| WO | 2007098355 A1 | 8/2007 |
| WO | 2007098359 A1 | 8/2007 |
| WO | 2008005618 A2 | 1/2008 |
| WO | 2008030999 A2 | 3/2008 |
| WO | 2008/131300 A2 | 10/2008 |
| WO | 2008137956 A2 | 11/2008 |
| WO | 2009/001309 A1 | 12/2008 |
| WO | 2008147600 A1 | 12/2008 |
| WO | 2009031161 A1 | 3/2009 |
| WO | 2009114837 A2 | 9/2009 |
| WO | 2009/124990 A1 | 10/2009 |
| WO | 2010015676 A1 | 2/2010 |
| WO | 2010/048449 A2 | 4/2010 |
| WO | 2010/132608 A2 | 11/2010 |
| WO | 2011036574 A1 | 3/2011 |
| WO | 2011143621 A1 | 11/2011 |
| WO | 2012/037213 A1 | 3/2012 |
| WO | 2012106266 A1 | 8/2012 |
| WO | 2012154277 A1 | 11/2012 |
| WO | 2012166746 A1 | 12/2012 |
| WO | 2012174109 A1 | 12/2012 |
| WO | 2013119557 A1 | 8/2013 |
| WO | 2013126446 A1 | 8/2013 |
| WO | 2013187827 A1 | 12/2013 |
| WO | 2014006403 A1 | 1/2014 |
| WO | 2014029424 A1 | 2/2014 |
| WO | 2014074417 A2 | 5/2014 |
| WO | 2014081942 A1 | 5/2014 |
| WO | 2014/123848 A1 | 8/2014 |
| WO | 2014120741 A1 | 8/2014 |
| WO | 2014133617 A1 | 9/2014 |
| WO | 2014140257 A1 | 9/2014 |
| WO | 2014140265 A1 | 9/2014 |
| WO | 2014/165783 A1 | 10/2014 |
| WO | 2014158908 A1 | 10/2014 |
| WO | 2014182421 A1 | 11/2014 |
| WO | 2014197656 A1 | 12/2014 |
| WO | 2014204593 A1 | 12/2014 |
| WO | 2015017136 A1 | 2/2015 |
| WO | 2015024904 A1 | 2/2015 |
| WO | 2015035393 A1 | 3/2015 |
| WO | 2015058136 A1 | 4/2015 |
| WO | 15108913 A1 | 7/2015 |
| WO | 2015/168655 A2 | 11/2015 |
| WO | 15164912 A1 | 11/2015 |
| WO | 2016/037127 A1 | 3/2016 |
| WO | 16178974 A1 | 11/2016 |
| WO | 2018/049413 A1 | 3/2018 |
| WO | 2018170349 A1 | 9/2018 |
| WO | 2019173641 A1 | 9/2019 |

OTHER PUBLICATIONS

U.S. Appl. No. 16/296,087, filed Mar. 7, 2019 Notice of Allowance dated Mar. 8, 2022.
U.S. Appl. No. 16/868,461, filed May 6, 2020 Non-Final Office Action dated Feb. 15, 2022.
U.S. Appl. No. 16/996,769, filed Aug. 18, 2020 Non-Final Office Action dated Mar. 2, 2022.
JP 2016-563441 filed Oct. 19, 2016 Office Action dated Jan. 25, 2019.
JP 2018-039302 filed Mar. 6, 2018 Office Action dated Feb. 20, 2019.
Menlo Care, Landmark™ Aquavene® Catheters Brochure, 1992.
Menlo Care, Landmark® Midline Catheter Maintenance and Reference Guide (1993).
Menlo Care, Landmark® Midline Catheters Brochure, 1991.
Menlo Care, Landmark® Venous Access Device Insertion Instructions (1992).
Menlo Care, Publications on Aquavene® Technology, Aug. 1992.
Notice of allowance dated Jan. 29, 2014 for U.S. Appl. No. 12/307,519.
Notice of allowance dated Jun. 10, 2015 for U.S. Appl. No. 11/577,491.
Office action dated Mar. 10, 2011 for U.S. Appl. No. 12/307,519.
Office action dated Mar. 15, 2011 for U.S. Appl. No. 11/577,491.
Office action dated Mar. 27, 2013 for U.S. Appl. No. 13/358,099.
Office action dated Aug. 2, 2010 for U.S. Appl. No. 11/577,491.
Office action dated Aug. 18, 2014 for U.S. Appl. No. 11/577,491.
Office action dated Oct. 25, 2010 for U.S. Appl. No. 12/307,519.

(56) References Cited

OTHER PUBLICATIONS

Office action dated Nov. 4, 2013 for U.S. Appl. No. 12/307,519.
Office action dated Mar. 12, 2015 for U.S. Appl. No. 11/577,491.
PCT/CN2017/075370 filed Mar. 1, 2017 International Search Report and Written Opinion dated Nov. 30, 2017.
PCT/US15/28950 filed May 1, 2015 International Search Report and Written Opinion dated Oct. 19, 2015.
PCT/US2008/062954 filed May 7, 2008 International search report and written opinion dated Jan. 16, 2009.
PCT/US2011/036530 filed May 13, 2011 International Search Report dated Oct. 6, 2011.
PCT/US2011/036530 filed May 13, 2011 Written Opinion of the International Searching Authority dated Oct. 6, 2011.
PCT/US2012/026618 International Preliminary Report on Patentability dated Aug. 27, 2013.
PCT/US2012/026618 International Search Report and Written Opinion dated Jun. 25, 2012.
PCT/US2013/073577 filed Dec. 6, 2013 International Search Report and Written Opinion dated Feb. 24, 2014.
PCT/US2014/013557 filed Jan. 29, 2014 International search report and written opinion dated Apr. 14, 2014.
PCT/US2015/048676 filed Sep. 4, 2015 International search report and written opinion dated Dec. 4, 2015.
PCT/US2016/032449 filed May 13, 2016 International Search Report and Written Opinion dated Oct. 5, 2016.
PCT/US2016/032534 filed May 13, 2016 International Search Report and Written Opinion dated Oct. 5, 2016.
PCT/US2017/051214 filed Sep. 12, 2017 International Search Report and Written Opinion dated Nov. 13, 2017.
PR Newswire, Luther Medical Products, Inc. Receives Approval to Supply Improved Neonatal Product to Japan, Aug. 20, 1998.
Rasor, Julia S, Review of Catheter-related infection rates: comparison of conventional catheter materials with Aquavene®, JVAN vol. 1, No. 3, Spring 1991.
RU 2017141812 filed Nov. 30, 2017 Office Action dated Jan. 31, 2018.
SG 11201709185X filed Nov. 8, 2017 Office Action dated Oct. 5, 2018.
SG 11201709193S filed Nov. 8, 2017 Office Action dated Oct. 5, 2018.
U.S. Appl. No. 12/598,053, filed Apr. 20, 2010 Notice of allowance dated Jan. 16, 2014.
U.S. Appl. No. 12/598,053, filed Apr. 20, 2010 Office action dated Aug. 28, 2013.
U.S. Appl. No. 12/598,053, filed Apr. 20, 2010 Office action dated Dec. 4, 2012.
U.S. Appl. No. 12/598,053, filed Apr. 20, 2010 Office action dated May 8, 2013.
U.S. Appl. No. 12/598,053, filed Apr. 20, 2010 Office action dated Oct. 24, 2013.
U.S. Appl. No. 13/107,781, filed May 13, 2011 Final Office Action dated Jul. 18, 2014.
U.S. Appl. No. 13/107,781, filed May 13, 2011 Non-Final Office Action dated Dec. 30, 2013.
U.S. Appl. No. 13/405,096, filed Feb. 24, 2012 Advisory Action dated Apr. 18, 2014.
U.S. Appl. No. 13/405,096, filed Feb. 24, 2012 Final Office Action dated Jan. 31, 2014.
U.S. Appl. No. 13/405,096, filed Feb. 24, 2012 Non-Final Office Action dated Aug. 20, 2013.
U.S. Appl. No. 13/405,096, filed Feb. 24, 2012 Non-Final Office Action dated Nov. 18, 2014.
U.S. Appl. No. 13/405,096, filed Feb. 24, 2012 Notice of Allowance dated Mar. 11, 2015.
U.S. Appl. No. 14/044,623, filed Oct. 2, 2013 Notice of Allowance dated Nov. 6, 2014.
U.S. Appl. No. 14/099,050, filed Dec. 6, 2013 Advisory Action dated Jun. 1, 2017.
U.S. Appl. No. 14/099,050, filed Dec. 6, 2013 Final Office Action dated Jan. 30, 2017.
PCT/US2019/021231 filed Mar. 7, 2019 International Search Report and Written Opinion, dated Jun. 27, 2019.
U.S. Appl. No. 14/250,093, filed Apr. 10, 2014 Notice of Allowance dated Aug. 19, 2020.
U.S. Appl. No. 14/866,738, filed Sep. 25, 2015 Notice of Allowance dated Sep. 24, 2020.
U.S. Appl. No. 15/869,872, filed Jan. 12, 2018 Advisory Action dated Sep. 23, 2020.
U.S. Appl. No. 16/292,076, filed Mar. 4, 2019 Non-Final Office Action dated Aug. 10, 2020.
U.S. Appl. No. 16/295,906, filed Mar. 7, 2019 Non-Final Office Action dated Sep. 4, 2020.
U.S. Appl. No. 29/654,521, filed Jun. 25, 2018 Notice of Allowability dated Sep. 30, 2020.
U.S. Appl. No. 29/654,521, filed Jun. 25, 2018 Notice of Allowance dated Aug. 17, 2020.
U.S. Appl. No. 29/654,527, filed Jun. 25, 2018 Notice of Allowability dated Sep. 30, 2020.
U.S. Appl. No. 29/654,527, filed Jun. 25, 2018 Notice of Allowance dated Aug. 18, 2020.
U.S. Appl. No. 29/658,136, filed Jul. 27, 2018 Non-Final Office Action dated Sep. 9, 2020.
U.S. Appl. No. 15/154,384, filed May 13, 2016 Restriction Requirement dated Jan. 25, 2019.
U.S. Appl. No. 15/154,808, filed May 13, 2016 Advisory Action dated Oct. 26, 2018.
U.S. Appl. No. 15/154,808, filed May 13, 2016 Final Office Action dated Aug. 16, 2018.
U.S. Appl. No. 15/154,808, filed May 13, 2016 Non-Final Office Action dated Apr. 6, 2018.
U.S. Appl. No. 15/154,808, filed May 13, 2016 Notice of Allowance dated Apr. 16, 2019.
U.S. Appl. No. 15/154,808, filed May 13, 2016 Restriction Requirement dated Jan. 3, 2018.
U.S. Appl. No. 15/377,880, filed Dec. 13, 2016 Final Office Action dated Oct. 19, 2018.
U.S. Appl. No. 15/377,880, filed Dec. 13, 2016 Non-Final Office Action dated May 14, 2018.
U.S. Appl. No. 15/481,773, filed Apr. 7, 2017 Final Office Action dated Jan. 10, 2019.
U.S. Appl. No. 15/481,773, filed Apr. 7, 2017 Non-Final Office Action dated Jun. 29, 2018.
U.S. Appl. No. 15/608,802, filed May 30, 2017 Non-Final Office Action dated Jun. 6, 2019.
U.S. Appl. No. 15/692,915, filed Aug. 31, 2017 Non-Final Office Action dated Jan. 29, 2018.
U.S. Appl. No. 15/702,537, filed Sep. 12, 2017 Final Office Action dated Mar. 8, 2019.
U.S. Appl. No. 15/702,537, filed Sep. 12, 2017 Non-Final Office Action dated Nov. 29, 2018.
U.S. Appl. No. 15/702,537, filed Sep. 12, 2017 Notice of Allowance dated Jul. 31, 2019.
U.S. Appl. No. 15/727,528, filed Oct. 6, 2017 Non-Final Office Action dated Sep. 20, 2019.
U.S. Appl. No. 15/727,528, filed Oct. 6, 2017 Restriction Requirement dated Aug. 7, 2019.
U.S. Appl. No. 15/862,380, filed Jan. 4, 2018 Restriction Requirement dated Dec. 23, 2019.
U.S. Appl. No. 15/951,931, filed Apr. 12, 2018 Non-Final Office Action dated Nov. 19, 2019.
U.S. Appl. No. 15/951,954, filed Apr. 12, 2018 Non-Final Office Action dated Nov. 4, 2019.
U.S. Appl. No. 29/536,043, filed Aug. 12, 2015 Final Office Action dated Mar. 26, 2018.
U.S. Appl. No. 29/536,043, filed Aug. 12, 2015 Non-Final Office Action dated Aug. 31, 2017.
U.S. Appl. No. 29/545,436, filed Nov. 12, 2015 Final Office Action dated Mar. 26, 2018.
U.S. Appl. No. 29/545,436, filed Nov. 12, 2015 Non-Final Office Action dated Sep. 12, 2017.
Waltimire, B. and Rasor, J.S., Midline catheter: Virtually bloodless insertion technique and needle safety tube minimize potential for transmission of bloodborne disease. Sponsored by national Foun-

(56) References Cited

OTHER PUBLICATIONS dation for Infectious Diseases. 5th National forum on AIDS, Hepatitis, and other blood-borne diseases. Atlanta, GA, Mar. 1992.
U.S. Appl. No. 15/862,380, filed Jan. 4, 2018 Final Office Action dated Oct. 26, 2020.
U.S. Appl. No. 16/295,906, filed Mar. 7, 2019 Final Office Action dated Dec. 22, 2020.
U.S. Appl. No. 15/154,384, filed May 13, 2016 Final Office Action dated Dec. 24, 2020.
U.S. Appl. No. 16/529,602, filed Aug. 1, 2019 Notice of Allowance dated Jan. 19, 2021.
U.S. Appl. No. 16/292,076, filed Mar. 4, 2019 Notice of Allowance dated Feb. 4, 2021.
U.S. Appl. No. 16/296,087, filed Mar. 7, 2019 Restriction Requirement dated Feb. 8, 2021.
U.S. Appl. No. 16/292,076, filed Mar. 4, 2019 Corrected Notice of Allowance dated Feb. 25, 2021.
U.S. Appl. No. 16/295,906, filed Mar. 7, 2019 Notice of Allowance dated Mar. 4, 2021.
U.S. Appl. No. 15/154,384, filed May 13, 2016 Notice of Allowance dated Mar. 17, 2021.
U.S. Appl. No. 16/389,719, filed Apr. 19, 2019 Non-Final Office Action dated Mar. 19, 2021.
U.S. Appl. No. 29/658,136, filed Jul. 27, 2018 Notice of Allowance dated Mar. 23, 2021.
Access Scientific, The PICC Wand® Product Data Sheet, Revision F, May 22, 2012.
Access Scientific, The Powerwand® Extended Dwell Catheter Brochure (http://accessscientific.com/media/4Fr-POWERWAND-Brochure.pdf) last accessed Sep. 25, 2015.
3D Angiocath™ Autoguard™ Shielded IV Catheter Brochure, © 2001.
3D Medical Systems, I.V. Catheter Family Brochure (2006).
BD Saf-T-Intima™ Integrated Safety IV Catheter Brochure, © 2001.
Becton Dickinson, Insyte® AutoGuard™ Shielded LV. Catheter Brochure, 1998.
CA 2,799,360 filed May 13, 2011 Office Action dated Jun. 7, 2017.
CN 201180029526.7 filed Dec. 14, 2012 First Office Action dated Apr. 21, 2014.
CN 2012800008866.6 filed Aug. 14, 2013 Second Office Action dated Aug. 17, 2015.
CN 201280008866.6 filed Aug. 14, 2013 First Office Action dated Dec. 31, 2014.
CN 201280008866.6 filed Aug. 14, 2013 Third Office Action dated Jan. 25, 2016.
CN 201380073657.4 filed Aug. 21, 2015 Office Action dated Jun. 28, 2017.
CN 201380073657.4 filed Aug. 21, 2015 Office Action dated Mar. 2, 2018.
CN 201480019467.9 filed Sep. 29, 2015 Office Action dated Apr. 6, 2017.
CN 201510079782.7 filed Feb. 13, 2015 Office Action dated Dec. 30, 2016.
CN 201510079782.7 filed Feb. 13, 2015 Office Action dated Feb. 5, 2018.
CN 201510079782.7 filed Feb. 13, 2015 Office Action dated Sep. 19, 2017.
CN 201580022407.7 filed Nov. 2, 2016 Office Action dated Jan. 31, 2019.
CN 201580022407.7 filed Nov. 2, 2016 Office Action dated Sep. 16, 2019.
Cook Medical "Lunderquist Extra-Stiff wire guide" (2012).
Endovascular Today "Coiled Stainless Steel Guidewires" Buyer's Guide pp. 13-20, (2012).
EP 07783404.2 filed Jan. 19, 2009 Office Action dated Apr. 16, 2019.
EP 07783404.2 filed Jan. 19, 2009 Office Action dated Mar. 7, 2018.
EP 10075422.5 filed Jul. 5, 2008 European search report and written opinion dated Dec. 1, 2010.
EP 11781384.0 filed Sep. 21, 2012 Extended European Search Report dated Oct. 31, 2017.
EP 12782187.4 filed Sep. 10, 2013 European search report and written opinion dated Aug. 30, 2016.
EP 12782187.4 filed Sep. 10, 2013 European search report and written opinion dated Dec. 17, 2015.
EP 12782187.4 filed Sep. 10, 2013 Office Action dated Apr. 24, 2018.
EP 12782187.4 filed Sep. 10, 2013 Office Action dated Nov. 28, 2018.
EP 13876666.2 filed Sep. 7, 2015 Extended European Search Report dated Sep. 20, 2016.
EP 15785819.2 filed Dec. 2, 2016 Extended European Search Report dated Dec. 4, 2017.
EP 16797029.2 filed Nov. 21, 2017 Extended European Search Report dated May 3, 2018.
EP 16797047.4 filed Dec. 6, 2017 Supplemental European Search Report dated Jan. 9, 2019.
EP 19181963.0 filed Jun. 24, 2019 Extended European Search Report dated Jul. 16, 2019.
European office action dated Apr. 21, 2008 for EP Application No. 06800027.2.
European office action dated Aug. 6, 2012 for EP Application No. 07783404.2.
European office action dated Oct. 5, 2010 for EP Application No. 07783404.2.
European search report and opinion dated Jul. 10, 2009 for EP Application No. 07783404.2.
Hadaway, Lynn C., A Midline Alternative to Central and Peripheral Venous Access, Caring Magazine, May 1990, pp. 45-50.
International search report and written opinion dated Apr. 2, 2012 for PCT/US2012/023192.
International search report and written opinion dated Jun. 1, 2007 for PCT/US2006/026671.
International search report and written opinion dated Oct. 23, 2008 for PCT/US2007/068393.
JP 2013-510353 filed Oct. 31, 2012 First Office Action dated Feb. 19, 2015.
JP 2013-510353 filed Oct. 31, 2012 Office Action dated Dec. 15, 2016.
JP 2013-510353 filed Oct. 31, 2012 Second Office Action dated Jan. 28, 2016.
JP 2015-560173 filed Aug. 28, 2015 Office Action dated Aug. 2, 2018.
JP 2015-560173 filed Aug. 28, 2015 Office Action dated Sep. 19, 2017.
JP 2016-107046 filed May 30, 2016 Office Action dated Apr. 26, 2017.
JP 2016-107046 filed May 30, 2016 Office Action dated Jul. 28, 2016.
JP 2016-107046 filed May 30, 2016 Office Action dated Nov. 7, 2017.
U.S. Appl. No. 14/099,050, filed Dec. 6, 2013 Non-Final Office Action dated Dec. 22, 2015.
U.S. Appl. No. 14/099,050, filed Dec. 6, 2013 Non-Final Office Action dated Jul. 19, 2016.
U.S. Appl. No. 14/099,050, filed Dec. 6, 2013 Notice of Allowance dated Sep. 14, 2017.
U.S. Appl. No. 14/099,050, filed Dec. 6, 2013 Notice of Panel Decision dated Aug. 1, 2017.
U.S. Appl. No. 14/167,149, filed Jan. 29, 2014 Non-Final Office Action dated Oct. 21, 2015.
U.S. Appl. No. 14/167,149, filed Jan. 29, 2014 Notice of Allowance dated Jul. 6, 2016.
U.S. Appl. No. 14/174,071, filed Feb. 6, 2014 Final Office Action dated Dec. 2, 2016.
U.S. Appl. No. 14/174,071, filed Feb. 6, 2014 Non-Final Office Action dated Jul. 29, 2016.
U.S. Appl. No. 14/174,071, filed Feb. 6, 2014 Non-Final Office Action dated Mar. 31, 2016.
U.S. Appl. No. 14/192,541, filed Feb. 27, 2014 Non-Final Office Action dated Jul. 20, 2016.

(56) References Cited

OTHER PUBLICATIONS

U.S. Appl. No. 14/192,541, filed Feb. 27, 2014 Notice of Allowance dated Dec. 6, 2016.
U.S. Appl. No. 14/192,541, filed Feb. 27, 2014 Notice of Corrected Allowability dated Mar. 8, 2017.
U.S. Appl. No. 14/250,093, filed Apr. 10, 2014 Advisory Action dated May 19, 2017.
U.S. Appl. No. 14/250,093, filed Apr. 10, 2014 Examiner's Answer dated Jun. 20, 2018.
U.S. Appl. No. 14/250,093, filed Apr. 10, 2014 Final Office Action dated Mar. 9, 2017.
U.S. Appl. No. 14/250,093, filed Apr. 10, 2014 Final Office Action dated Nov. 6, 2017.
U.S. Appl. No. 14/250,093, filed Apr. 10, 2014 Non-Final Office Action dated Nov. 16, 2016.
U.S. Appl. No. 14/250,093, filed Apr. 10, 2014 Panel Decision dated Jul. 14, 2017.
U.S. Appl. No. 14/477,717, filed Sep. 4, 2014, Notice of allowance dated Feb. 17, 2015.
U.S. Appl. No. 14/477,717, filed Sep. 4, 2014, Office action dated Dec. 18, 2014.
U.S. Appl. No. 14/585,800, filed Dec. 30, 2014 Final Office Action dated May 11, 2018.
U.S. Appl. No. 14/585,800, filed Dec. 30, 2014 Non-Final Office Action dated May 16, 2016.
U.S. Appl. No. 14/585,800, filed Dec. 30, 2014 Non-Final Office Action dated Nov. 29, 2016.
U.S. Appl. No. 14/585,800, filed Dec. 30, 2014 Non-Final Office Action dated Nov. 3, 2017.
U.S. Appl. No. 14/585,800, filed Dec. 30, 2014 Non-Final Office Action dated Oct. 8, 2015.
U.S. Appl. No. 14/585,800, filed Dec. 30, 2014 Notice of Allowance dated Feb. 25, 2019.
U.S. Appl. No. 14/585,800, filed Dec. 30, 2014 Notice of Allowance dated Jul. 3, 2017.
U.S. Appl. No. 14/702,580, filed May 1, 2015 Advisory Action dated Nov. 13, 2017.
U.S. Appl. No. 14/702,580, filed May 1, 2015 Final Office Action dated Sep. 1, 2017.
U.S. Appl. No. 14/702,580, filed May 1, 2015 Non-Final Office Action dated May 3, 2017.
U.S. Appl. No. 14/702,580, filed May 1, 2015 Notice of Allowance dated Dec. 8, 2017.
U.S. Appl. No. 14/750,658, filed Jun. 25, 2016 Non-Final Office Action dated Mar. 9, 2017.
U.S. Appl. No. 14/750,658, filed Jun. 25, 2016 Notice of Allowance dated Jul. 20, 2017.
U.S. Appl. No. 14/846,387, filed Sep. 4, 2015 Advisory Action dated May 10, 2018.
U.S. Appl. No. 14/846,387, filed Sep. 4, 2015 Final Office Action dated Mar. 22, 2018.
U.S. Appl. No. 14/846,387, filed Sep. 4, 2015 Non-Final Office Action dated Sep. 22, 2017.
U.S. Appl. No. 14/846,387, filed Sep. 4, 2015 Notice of Allowance dated Oct. 29, 2018.
U.S. Appl. No. 14/866,441, filed Sep. 25, 2015 Advisory Action dated Dec. 22, 2016.
U.S. Appl. No. 14/866,441, filed Sep. 25, 2015 Final Office Action dated Jun. 5, 2018.
U.S. Appl. No. 14/866,441, filed Sep. 25, 2015 Final Office Action dated Sep. 23, 2016.
U.S. Appl. No. 14/866,441, filed Sep. 25, 2015 Non-Final Office Action dated Apr. 7, 2017.
U.S. Appl. No. 14/866,441, filed Sep. 25, 2015 Non-Final Office Action dated Mar. 14, 2016.
U.S. Appl. No. 14/866,441, filed Sep. 25, 2015 Notice of Allowance dated Oct. 17, 2018.
U.S. Appl. No. 14/866,738, filed Sep. 25, 2015 Final Office Action dated Feb. 24, 2017.
U.S. Appl. No. 14/866,738, filed Sep. 25, 2015 Non-Final Office Action dated Nov. 6, 2017.
U.S. Appl. No. 14/866,738, filed Sep. 25, 2015 Non-Final Office Action dated Oct. 31, 2016.
U.S. Appl. No. 14/866,738, filed Sep. 25, 2015 Notice of Panel Decision dated Jun. 23, 2017.
U.S. Appl. No. 14/876,735, filed Oct. 6, 2015 Non-Final Office Action dated Mar. 30, 2017.
U.S. Appl. No. 15/154,384, filed May 13, 2016 Final Office Action dated Nov. 27, 2019.
U.S. Appl. No. 15/154,384, filed May 13, 2016 Non-Final Office Action dated Jun. 28, 2019.
U.S. Appl. No. 16/296,087, filed Mar. 7, 2019 Final Office Action dated Sep. 10, 2021.
U.S. Appl. No. 16/450,800, filed Jun. 24, 2019 Notice of Allowance dated Nov. 3, 2021.
U.S. Appl. No. 16/490,023, filed Aug. 29, 2019 Non-Final Office Action dated Oct. 4, 2021.
U.S. Appl. No. 15/154,384, filed May 13, 2016 Notice of Allowance dated Apr. 29, 2021.
U.S. Appl. No. 15/862,380, filed Jan. 4, 2018 Notice of Allowance dated Jun. 16, 2021.
U.S. Appl. No. 16/296,087, filed Mar. 7, 2019 Non-Final Office Action dated Mar. 26, 2021.
U.S. Appl. No. 16/389,719, filed Apr. 19, 2019 Final Office Action dated Jun. 14, 2021.
U.S. Appl. No. 16/450,800, filed Jun. 24, 2019 Non-Final Office Action dated Jul. 9, 2021.
U.S. Appl. No. 16/490,023, filed Aug. 29, 2019 Restriction Requirement dated May 4, 2021.
U.S. Appl. No. 16/529,622, filed Aug. 1, 2019 Non-Final Office Action dated May 7, 2021.
U.S. Appl. No. 16/529,622, filed Aug. 1, 2019 Notice of Allowance dated Aug. 23, 2021.
EP 22192364.2 filed Aug. 26, 2022 Extended European Search Report dated Nov. 30, 2022.
U.S. Appl. No. 16/867,349, filed May 5, 2020 Final Office Action dated Dec. 28, 2022.
U.S. Appl. No. 16/868,461, filed May 6, 2020 Examiner's Answer dated Jan. 31, 2023.
U.S. Appl. No. 16/902,031, filed Jun. 15, 2020 Non-Final Office Action dated Dec. 21, 2022.
U.S. Appl. No. 17/164,653, filed Feb. 1, 2021, Notice of Allowance dated Nov. 1, 2022.
U.S. Appl. No. 17/471,051, filed Sep. 9, 2021 Restriction Requirement dated Dec. 22, 2021.
U.S. Appl. No. 17/863,179, filed Jul. 12, 2022 Non-Final Office Action dated Dec. 7, 2022.
EP 22159383.3 filed Mar. 1, 2022 Extended European Search Report dated May 30, 2022.
PCT/US2019/052225 filed Sep. 20, 2019 International Search Report and Written Opinion dated Jun. 25, 2020.
PCT/US2020/046860 filed Aug. 18, 2020 International Search Report and Written Opinion dated Nov. 18, 2020.
U.S. Appl. No. 16/490,023, filed Aug. 29, 2019 Notice of Allowance dated Mar. 14, 2022.
U.S. Appl. No. 16/867,349, filed May 5, 2020 Non-Final Office Action dated Jun. 16, 2022.
U.S. Appl. No. 16/868,461, filed May 6, 2020 Final Office Action dated May 25, 2022.
U.S. Appl. No. 16/996,769, filed Aug. 18, 2020 Notice of Allowance dated Jun. 13, 2022.
U.S. Appl. No. 17/164,653, filed Feb. 1, 2021, Restriction Requirement dated Sep. 7, 2022.
U.S. Appl. No. 17/337,273, filed Jun. 2, 2021 Notice of Allowance dated Oct. 5, 2022.
EP 16797029.2 filed Nov. 21, 2017 Office Action dated Mar. 27, 2020.
EP17849786.3 filed Apr. 12, 2019 Extended European Search Report dated May 13, 2020.
U.S. Appl. No. 14/250,093, filed Apr. 10, 2014 Patent Board Decision dated Jun. 8, 2020.

(56) References Cited

OTHER PUBLICATIONS

U.S. Appl. No. 14/866,738, filed Sep. 25, 2015 Patent Board Decision—Examiner Affirmed in Part dated Jul. 13, 2020.
U.S. Appl. No. 15/154,384, filed May 13, 2016 Non-Final Office Action dated Jun. 26, 2020.
U.S. Appl. No. 15/727,528, filed Oct. 6, 2017 Final Office Action dated Jan. 28, 2020.
U.S. Appl. No. 15/727,528, filed Oct. 6, 2017 Notice of Allowance dated Mar. 27, 2020.
U.S. Appl. No. 15/862,380, filed Jan. 4, 2018 Non-Final Office Action dated Jul. 9, 2020.
U.S. Appl. No. 15/869,872, filed Jan. 12, 2018 Final Office Action dated Jun. 25, 2020.
U.S. Appl. No. 15/869,872, filed Jan. 12, 2018 Non-Final Office Action dated Apr. 10, 2020.
U.S. Appl. No. 15/951,931, filed Apr. 12, 2018 Notice of Allowance dated Feb. 20, 2020.
U.S. Appl. No. 15/951,931, filed Apr. 12, 2018 Notice of Allowability dated Apr. 16, 2020.
U.S. Appl. No. 15/951,954, filed Apr. 12, 2018 Notice of Allowance dated Feb. 23, 2020.
U.S. Appl. No. 15/951,954, filed Apr. 12, 2018 Notice of Allowability dated Apr. 7, 2020.
U.S. Appl. No. 16/138,523, filed Sep. 21, 2018 Notice of Allowance dated Mar. 26, 2020.
U.S. Appl. No. 29/654,521, filed Jun. 25, 2018 Restriction Requirement dated Apr. 8, 2020.
U.S. Appl. No. 29/654,527, filed Jun. 25, 2018 Restriction Requirement dated Mar. 10, 2020.
U.S. Appl. No. 29/658,136, filed Jul. 27, 2018 Restriction Requirement dated May 11, 2020.
U.S. Appl. No. 17/353,602, filed Jun. 21, 2021 Non-Final Office Action dated Mar. 30, 2023.
U.S. Appl. No. 17/471,051, filed Sep. 9, 2021 Non-Final Office Action dated May 24, 2023.
U.S. Appl. No. 18/094,917, filed Jan. 9, 2023 Non-Final Office Action dated Jun. 8, 2023.

* cited by examiner

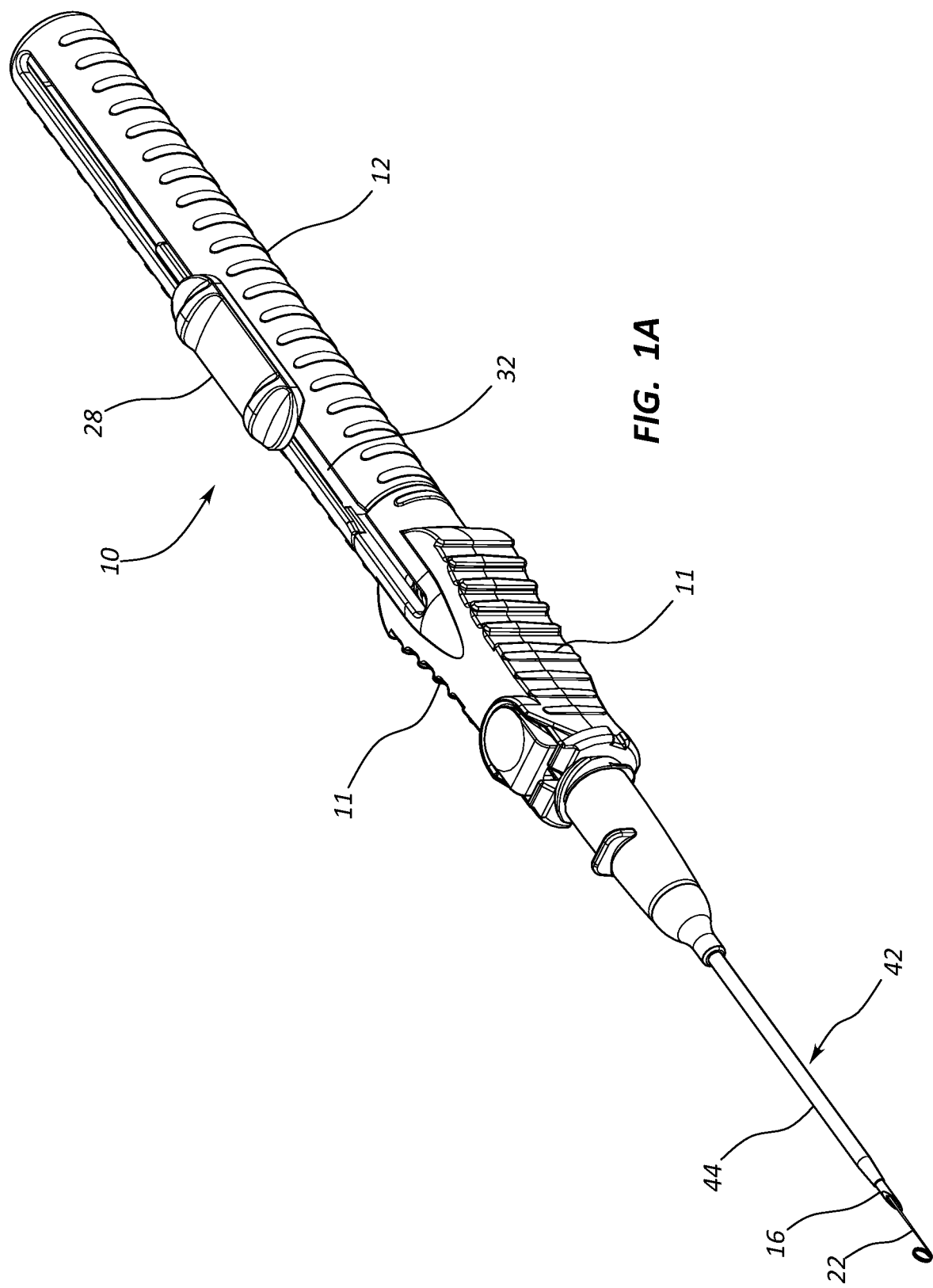

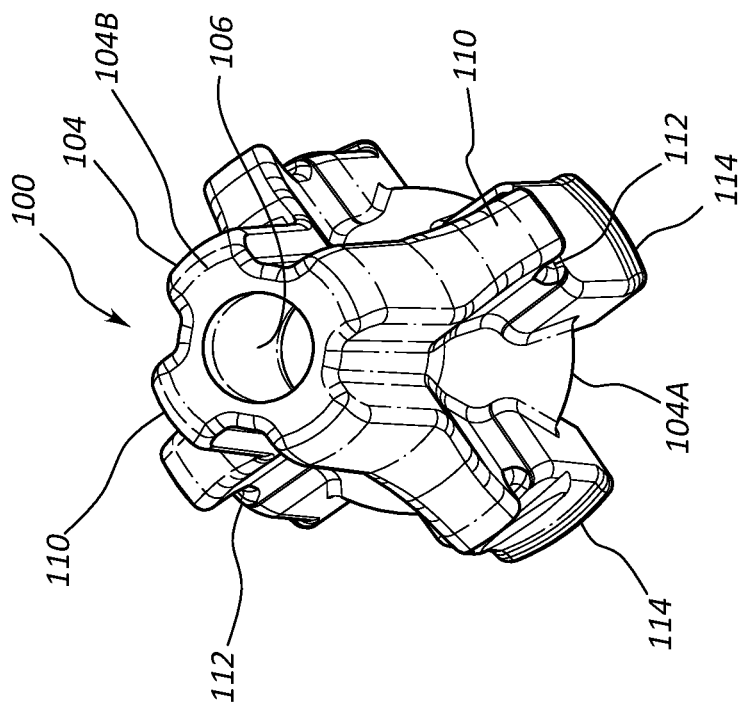
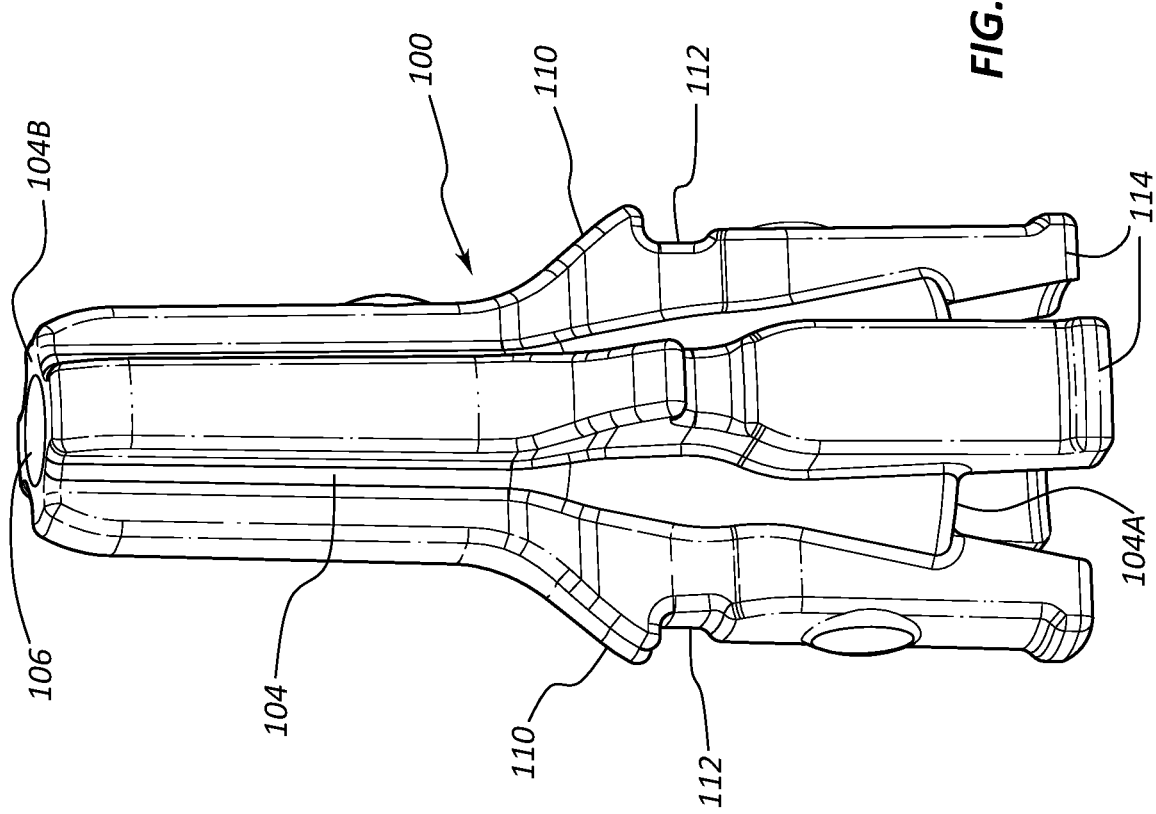
FIG. 5B
FIG. 5A

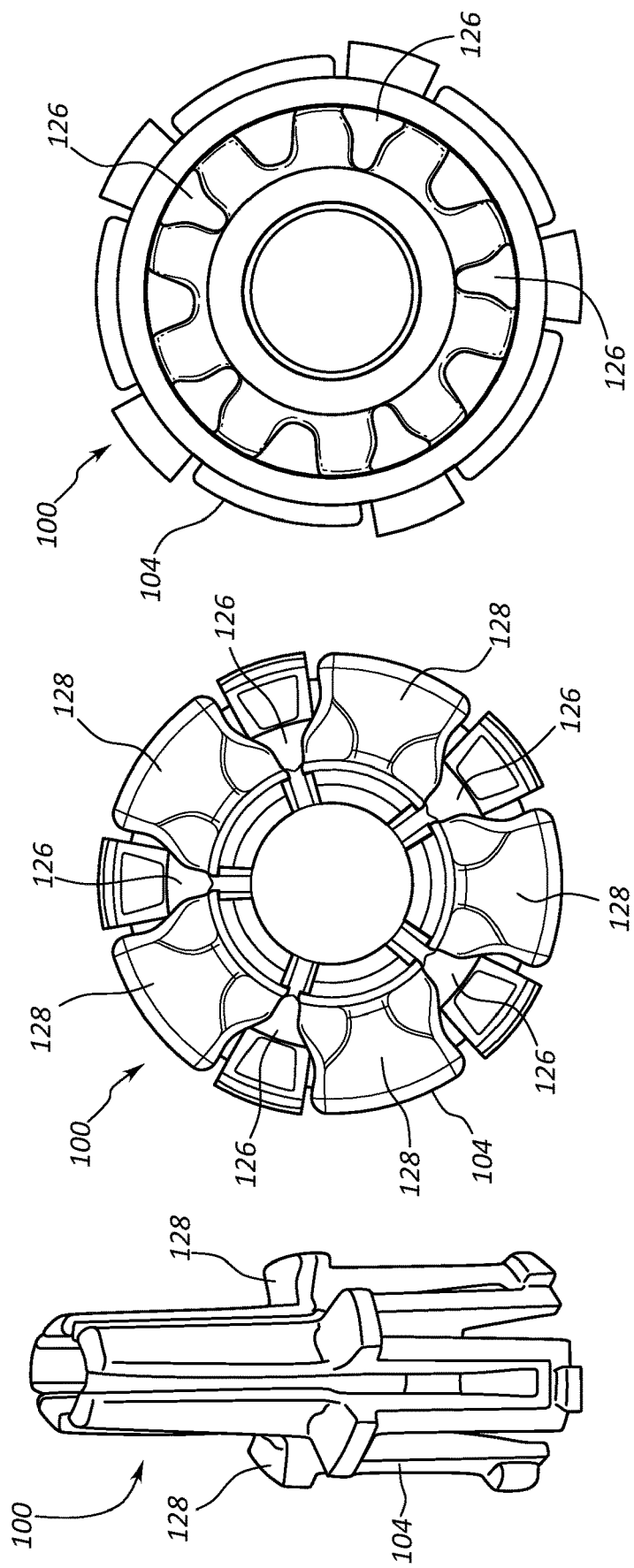

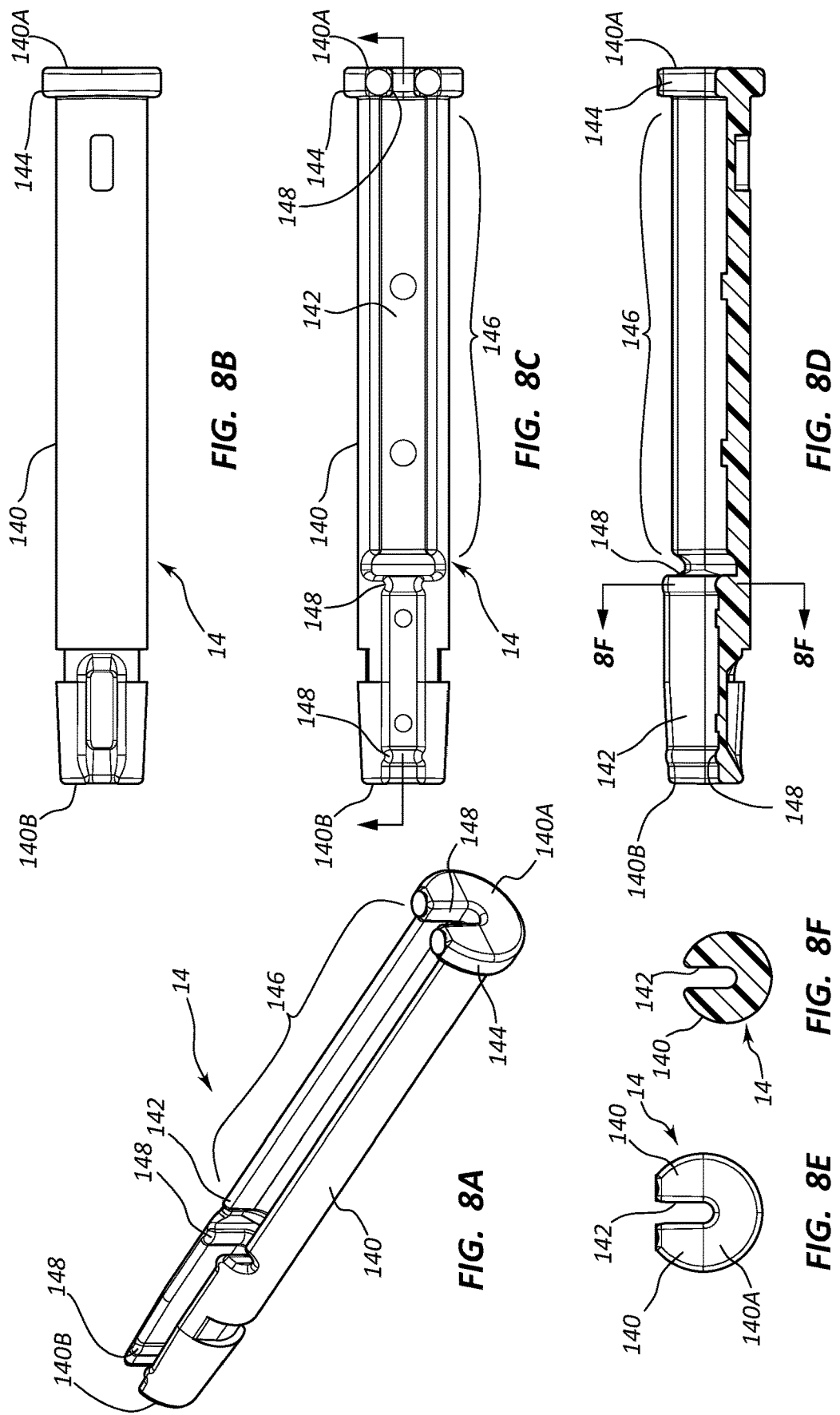

BLOOD CONTROL FOR A CATHETER INSERTION DEVICE

CROSS-REFERENCE TO RELATED APPLICATIONS

This application is a division of U.S. patent application Ser. No. 15/702,537, filed Sep. 12, 2017, now U.S. Pat. No. 10,493,262, which claims the benefit of U.S. Provisional Patent Application No. 62/393,531, filed Sep. 12, 2016, and titled "BLOOD CONTROL FOR A CATHETER INSERTION DEVICE," each of which is incorporated herein by reference in its entirety.

BRIEF SUMMARY

Briefly summarized, embodiments of the present invention are directed to a tool for assisting with the placement into a patient of a catheter or other tubular medical device. In particular, a fluid control component configured for controlling fluid flow through the hub of the catheter assembly during and after placement into the patient is disclosed.

In one embodiment, the fluid control component comprises a body disposed within a cavity of the hub, the body being movable between a first position and a second position, wherein the body does not pierce a valve disposed in the hub when in the first position and wherein the body pierces the valve when in the second position. The body includes a conduit to enable fluid flow through an internal portion of the body when the body is in the second position, and a plurality of longitudinally extending ribs disposed on an exterior surface of the body. The ribs provide at least one fluid flow channel between the valve and an external portion of the body when the body is in the second position.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIGS. 1A and 1B are perspective views of a catheter insertion device according to one embodiment;

FIGS. 5A and 5B show various views of the blood control component of FIG. 4;

FIGS. 6A-6C show various views of a blood control component for a catheter according to one embodiment;

FIGS. 8A-8F show various views of a needle hub of the catheter insertion device of FIGS. 1A and 1B;

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

Embodiments of the present invention are generally directed to a tool for assisting with the placement into a patient of a catheter or other tubular medical device. For example, catheters of various lengths are typically placed into a body of a patient so as to establish access to the patient's vasculature and enable the infusion of medicaments or aspiration of body fluids. The catheter insertion tool to be described herein facilitates such catheter placement. Note that, while the discussion below focuses on the placement of catheters of a particular type and relatively short length, catheters of a variety of types, sizes, and lengths can be inserted via the present device, including peripheral IVs, intermediate or extended-dwell catheters, PICCs, central venous catheters, etc. In one embodiment, catheters having a length between about 1.25 inch and about 2.25 inches can be placed, though many other lengths are also possible.

Figure 1B:
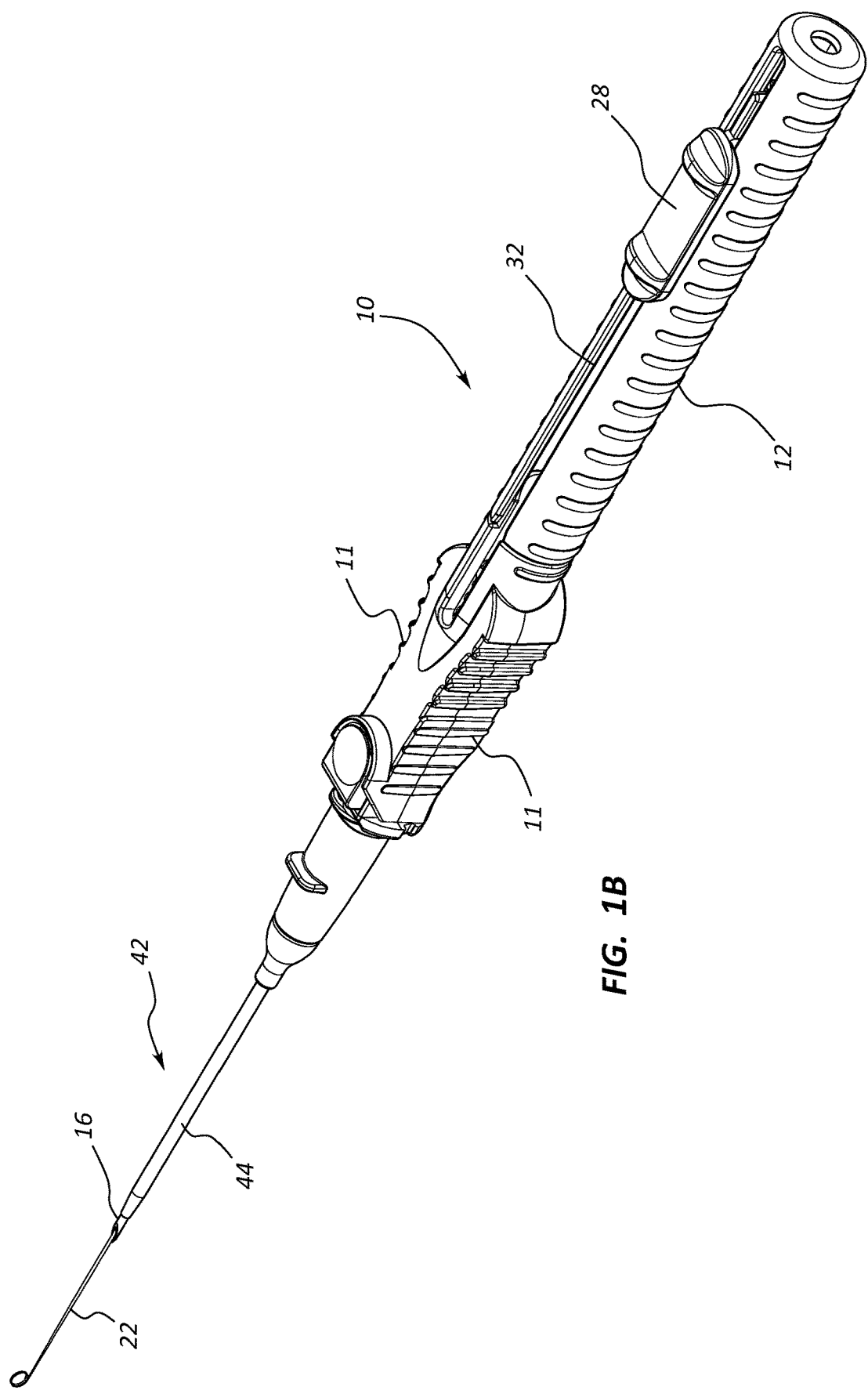
Figure 2:
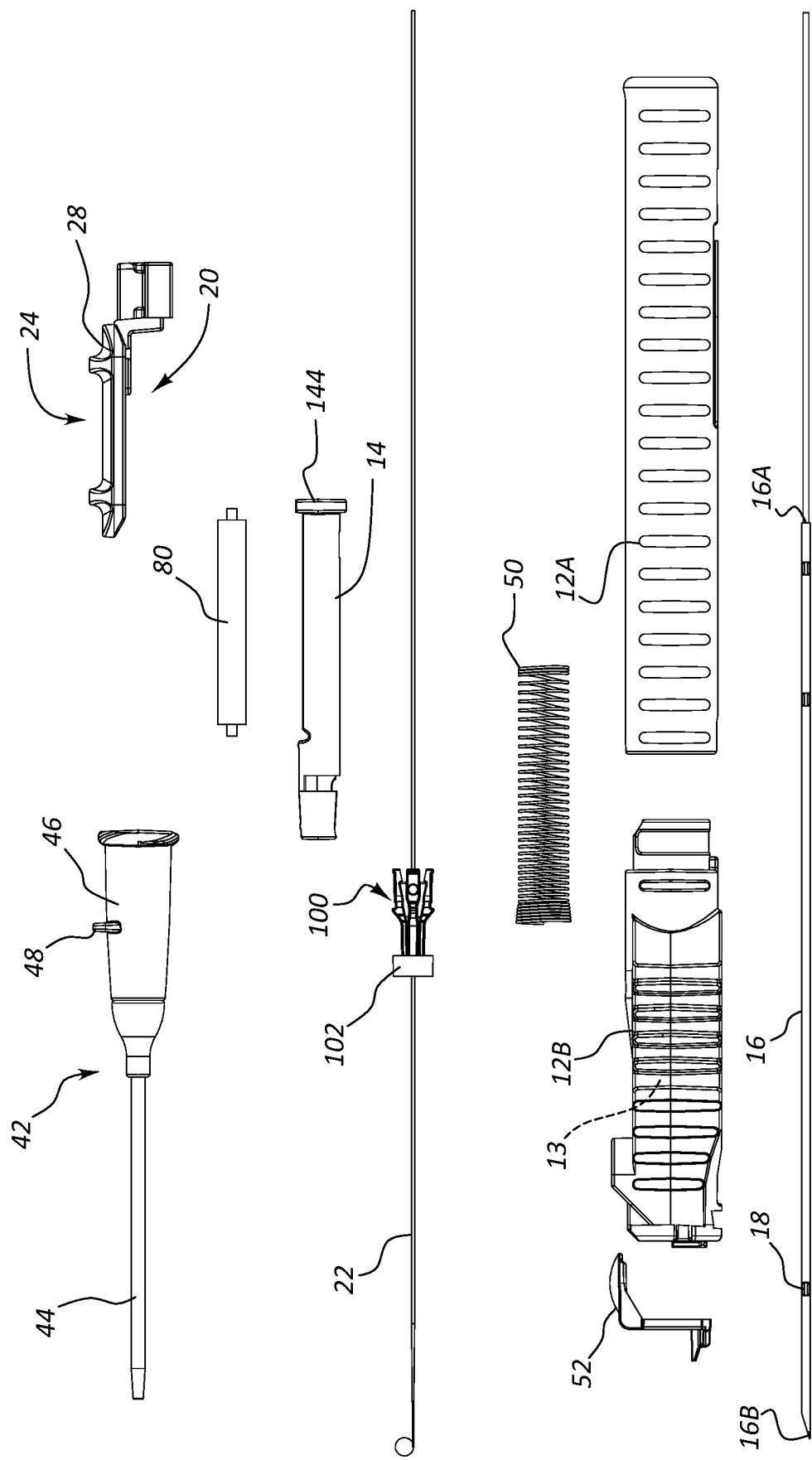
FIG. 2 is an exploded view of the catheter insertion device of FIGS. 1A and 1B.

FIGS. 1A-2 depict various details regarding a catheter insertion tool ("insertion tool" or "insertion device"), generally depicted at 10, according to one embodiment. As shown, the insertion tool 10 includes a housing 12 that may itself include a proximal housing portion 12A and a distal housing portion 12B. The housing 12 further includes an open distal end, and can include a flat bottom to enable the insertion device 10 to lie flat on a surface without tipping. In another embodiment, the housing is integrally formed. In yet another embodiment, a top housing portion and a bottom housing portion can be employed, or more than two portions can be used. In the present embodiment, the housing composed of a thermoplastic such as polycarbonate and is translucent, though other configurations are contemplated. The housing 12 defines grip surfaces 13 on either side of the housing, as seen in FIGS. 1A and 1B, to enable grasping of the insertion device 10 by the user.

A needle hub 14 supporting a hollow needle 16 (which together form part of a needle assembly, in one embodiment) is included with the housing 12. In the present embodiment, the needle hub 14 is secured within the housing 12 within a cavity 13 defined by the housing, but in another embodiment it can be integrally formed with the housing.

As will be described in detail further below, the needle hub 14 includes a slot for receiving a portion of the needle 16 and a quantity of adhesive, such as liquid or UV-cure adhesive for example, in order to fix the needle in place in the needle hub. The needle 16 extends distally from the needle hub 14 so as to extend past the distal end of the distal housing portion 12B and terminates at a distal end 16B thereof. A notch 18 is defined through the wall of the needle 16 proximate the distal end thereof. The notch 18 enables flashback of blood to exit the lumen defined by the hollow needle 16 once access to the patient's vasculature is achieved during catheter insertion procedures. Thus, blood exiting the notch 18 can be viewed by a clinician to confirm proper needle placement in the vasculature, as will be explained further below.

A catheter 42 including a catheter tube 44 is removably disposed on the portion of the needle 16 residing external to the housing 12 such that the needle occupies a lumen of the catheter defined by a catheter tube. The catheter tube 44 extends distally from a hub 46 of the catheter 42, which hub is initially disposed adjacent the open distal end of the distal housing portion 12B, as shown in FIGS. 1A and 1B.

The insertion device 10 further includes a guidewire advancement assembly 20 for advancing a guidewire 22 through the needle 16 and into the vasculature of the patient once vessel access by the needle has been achieved. The guidewire 22 (FIGS. 1A-2) is pre-disposed within the lumen of the needle 16. The guidewire advancement assembly 20 includes a guidewire lever 24 that selectively advances the guidewire 22 in a distal direction during use of the insertion device 10 such that the distal portion of the guidewire extends beyond the distal end 16B of the needle 16. In the present embodiment, a finger pad 28 of the guidewire lever 24 is slidably disposed on the housing 12 via a slot 32 to enable a thumb and/or finger(s) of the user to selectively advance the guidewire 22 distally past the distal end 16B of the needle 16. Of course, other engagement schemes to translate user input to guidewire movement could also be employed. In one embodiment, the guidewire 22 can include a guidewire support tube to provide additional stiffness to the guidewire and facilitate its distal advancement described above. In yet another embodiment, a proximal end of the guidewire can be attached at an anchor point on an interior portion of the housing 12 (or other fixed portion of the insertion device 10) and looped about a proximal portion of the guidewire lever 24 in a roughly U-shaped configuration such that the distal end of the guidewire extends two units of distance distally past the distal end 16B of the needle 16 for every one unit of distance of movement of the finger pad 28. These and other modifications are therefore contemplated.

The majority length of the guidewire in one embodiment includes a metal alloy of nickel and titanium commonly referred to as nitinol, though other suitable guidewire materials can also be employed.

FIGS. 1A and 1B show that the catheter 42 is removably attached to the insertion device 10 such that the catheter tube 44 thereof is disposed over the portion of the needle 16 that extends distal to the housing 12 such that the catheter resides external to the insertion device housing. The catheter 42 in the present embodiment is kept in place against the open distal end of the housing via a friction fit with one or more features disposed on the housing distal end. A tab 48 is included on the catheter hub 46 for assisting with manual distal extension of the catheter 42 by a user during deployment thereof.

Note that in one embodiment the outer diameters (and/or other areas) of the needle 16 and the catheter tube 44 are lubricated with silicone or other suitable lubricant to enhance sliding of the catheter tube with respect to the needle and for aiding in the insertion of the catheter into the body of the patient.

The insertion device 10 includes a retraction system configured to selectively retract the needle 16 into the housing 12. In detail, a spring element, such as a coil spring 50, is disposed between a distal end of the inner cavity 13 of the housing 12 and a ridge 144 disposed at a proximal end of the needle hub 14. The spring 50 is disposed about the needle hub 14, and the needle hub is proximally slidable within the cavity of the housing 12. The needle hub 14 is kept in a distal position within the cavity of the housing 12, with the spring maintained in a compressed configuration, by a retraction button 52 disposed near the distal end of the housing 12. Manual depression of the retraction button 52 releases engagement of the retraction button with the needle hub 14, which in turn enables the spring 50 to expand, causing the needle hub to move proximally within the cavity of the housing 12. This in turn retracts the needle 16 so that the distal end 16B thereof is retracted into the housing 12 and protected from inadvertent contact by a user. Note that other needle safety configurations can also be employed.

Use of the insertion device 10 in placing the catheter 42 in the vasculature of a patient is described here. A user grasping the insertion device 10 first guides the distal portion of the needle 16 through the skin at a suitable insertion site and accesses a subcutaneous vessel. After needle access to the vessel is confirmed, the guidewire advancement assembly 20 is actuated, wherein the finger pad 28 (disposed in the slot 32 defined in the housing 12) is advanced by the finger of the user to distally advance the guidewire 22 (FIG. 3A), initially disposed within the hollow needle 16. Note that the guidewire 22 is distally advanced by the guidewire lever 24, which is operably attached to the slidable finger pad 28.

Distal advancement of the guidewire 22 continues until the finger pad 28 has been distally slid a predetermined distance, resulting in a predetermined length of the guidewire 22 extending past the distal end of the needle 16, as shown in FIGS. 1A and 1B. This places the distal portion of the guidewire 22 within the vessel.

Once the guidewire lever 24 has been fully distally extended via sliding of the finger pad 28, which in turn has extended the guidewire 22 past the distal end 16B of the needle 16, manual distal advancement of the catheter 42 is performed, using the tab 48 of the catheter hub 46, which causes the catheter tube 44 to slide over distal portions of the needle 16 and guidewire 22 and into the patient's vasculature via the insertion site. In light of this, it is appreciated that the finger pad 28 acts as a first member used to advance the guidewire 22, whereas manual advancement is employed to advance the catheter 42, in the present embodiment. In another embodiment, it is appreciated that the finger pad 28 can be employed to also distally deploy the catheter 42 at least a partial distance into the vessel.

The catheter 42 is distally advanced until it is suitably disposed within the vessel of the patient. The retraction button 52 on the housing 12 is then manually depressed by the user, which causes the spring 50 to decompress and retract the needle hub 14, which in turn causes the distal end 16B of the needle 16 to be retracted within the housing 12 and preventing its re-emergence, thus protecting the user from accidental needle sticks. Thus, this serves as one example of a needle safety component, according to the present embodiment; others are possible. The catheter 42 is physically separated from the housing 12 at this time. Now in place within the patient, the catheter 42 can be prepared for use and dressed, per standard procedures. Then insertion device 10 can be discarded.

Figure 9:
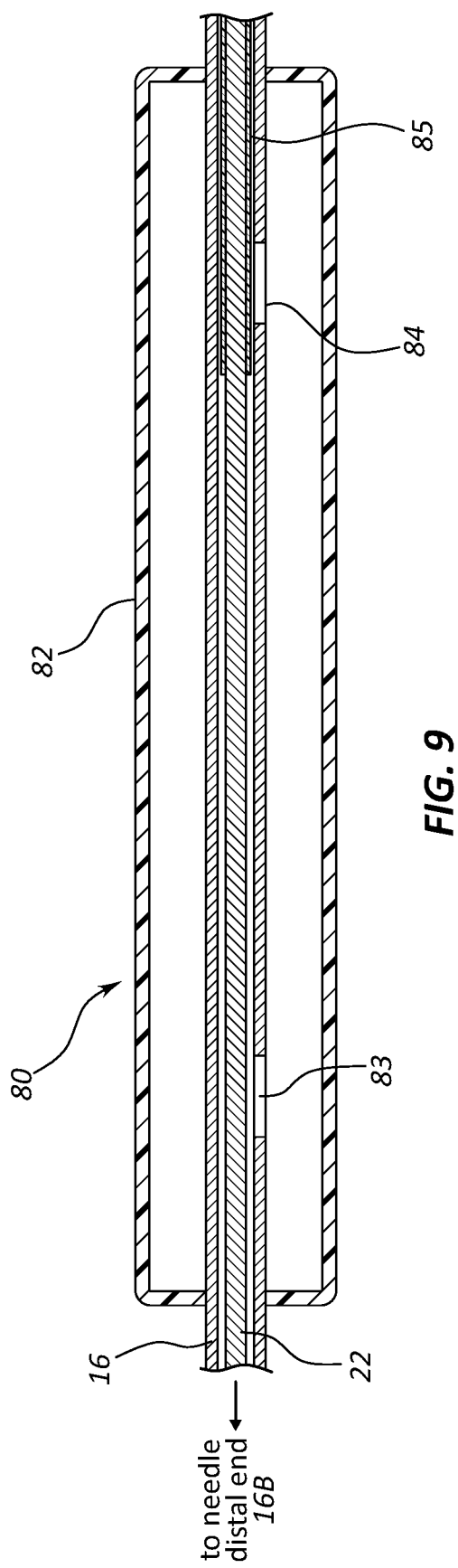
FIG. 9 is a cross sectional view of a flash indicator of the catheter insertion device of FIGS. 1A and 1B.

In additional detail, FIG. 2 shows a continuous blood flash indicator 80 that can be used with the insertion device 10 according to one embodiment. The flash indicator 80 is employed to indicate the presence of blood in the lumen of the needle 16 during use of the device 10, thus assuring that proper access has been made by the needle into a vein or other desired blood-carrying vessel. As shown in FIG. 9, the flash indicator 80 includes a translucent chamber 82 that is generally cylindrical in shape, sealed at either end, and disposed about a portion of the needle 16 such that the needle protrudes out from either sealed end. In the present embodiment the chamber 82 of the flash indicator 80 is disposed in the slot 142 (FIGS. 8A-8F) of the needle hub 14 within the housing 12, though other locations along the needle are also possible.

Two notches—a first notch 83 and a second notch 84—are defined in the needle 16 so as to provide fluid communication between the lumen of the needle and the interior of the flash indicator chamber. The notches 83, 84 replace the notch 18 (FIG. 2) in one embodiment, and are included in addition to the notch 18, in another embodiment. It is appreciated that, in one embodiment, blood passage through the notch 18 serves as an initial indicator that the distal end 16B of the needle has entered the vein, while the embodiment shown here serves as an additional indicator to verify that the needle distal end remains in the vein after initial access. Further detail regarding the flash indicator 80 can be found in U.S. Publication No. 2016/0331938, published Nov. 17, 2016, and entitled "Catheter Placement Device Including an Extensible Needle Safety Component," which is incorporated herein by reference in its entirety.

In the present embodiment, the guidewire 22 passes through the lumen of the needle 16 so as to extend through the flash indicator 80. The first notch 83 is disposed distal to the second notch 84 toward the distal end of the chamber 82.

When vessel access is achieved by the distal end 16B of the needle 16, blood travels proximally up the lumen of the needle, between the inner surface of the needle and the outer surface of the guidewire 22, disposed in the needle lumen (FIG. 9). Upon reaching the relatively more distal first notch 83 defined in the needle 16, a portion of the blood will pass through the first notch and enter the chamber 82. As the blood fills the translucent chamber 82, a user can observe the chamber through the translucent housing 12 of the insertion device 10 and view the blood therein, thus confirming that the vessel access has been achieved. In another embodiment, the housing 12 can be configured such that direct viewing of the chamber 82 is possible, e.g., with no intervening structure interposed between the chamber and the user.

The second notch 84 is employed to provide an exit point for air in the chamber 82 to equalize air pressure and enable the blood to continue entering the chamber via the first notch 83. It is noted that the spacing between the inner surface of the needle 16 and the outer surface of the guidewire 22 along section 85 is such that air but not blood can pass therebetween, thus enabling air pressure equalization in the chamber without blood passage through the second notch 84. In this way, the flash indicator 80 is a continuous indicator, enabling a continuous flow of blood into the chamber 82 while the needle distal end 16B is disposed within the blood-carrying vessel.

Note that the catheter insertion device 10 can include more than one flash indicator. In one embodiment and as mentioned above, for instance, the blood flash indicator 80 can be included, along with another flash indicator, such as the notch 18, which enables blood present in the lumen of the needle 16 to proceed proximally up the space between the outer surface of the needle and the inner surface of the catheter 42.

Figure 3:
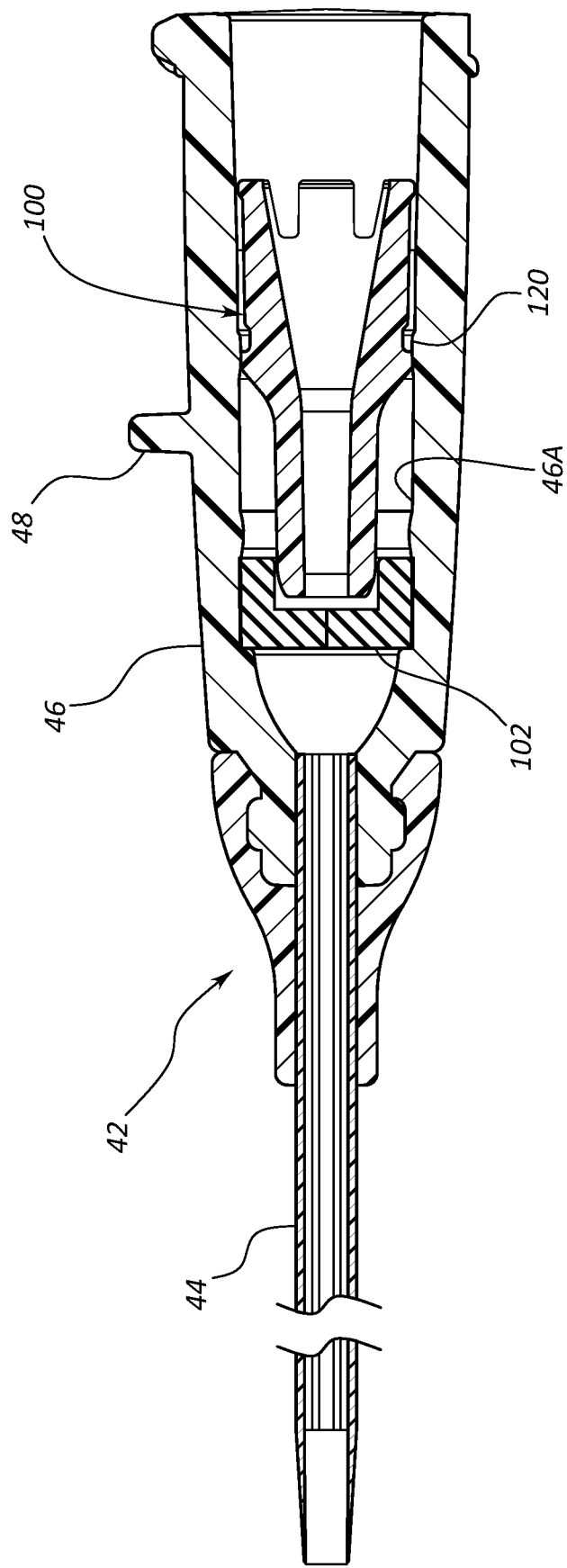
FIG. 3 is a cross-sectional side view of a catheter according to one embodiment.
Figure 10:
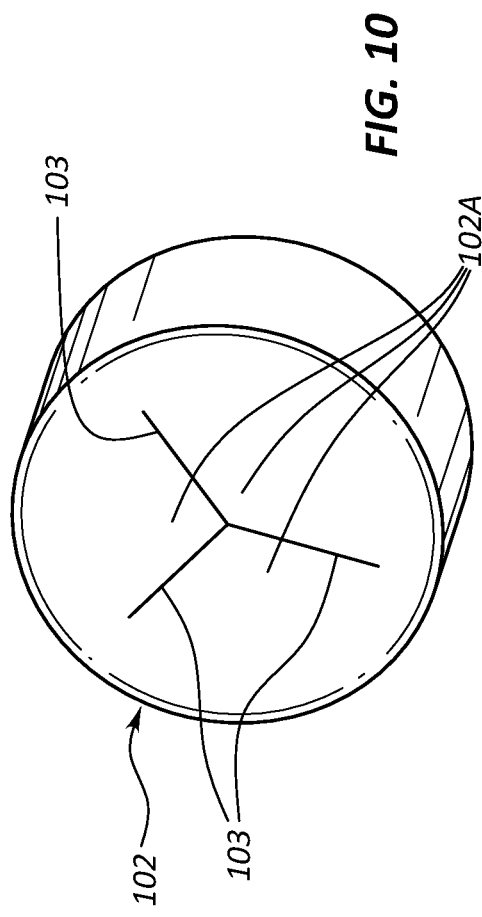
FIG. 10 is a perspective view of a valve of the catheter insertion device of FIGS. 1A and 1B.

FIG. 3 depicts various details of a blood control component 100 included with the catheter 42, in accordance with one embodiment. As shown, the blood component 100 is slidably disposed within a cavity 46A of the catheter hub 46 and is configured to selectively enable fluid flow through the catheter 42 in concert with a valve 102, also disposed within the catheter hub cavity. The valve 102 in the present embodiment is a tricuspid valve including three leaflets 102A defined by a plurality of slits 103 as seen in FIG. 10, though other valve types may also be employed.

Figure 4:
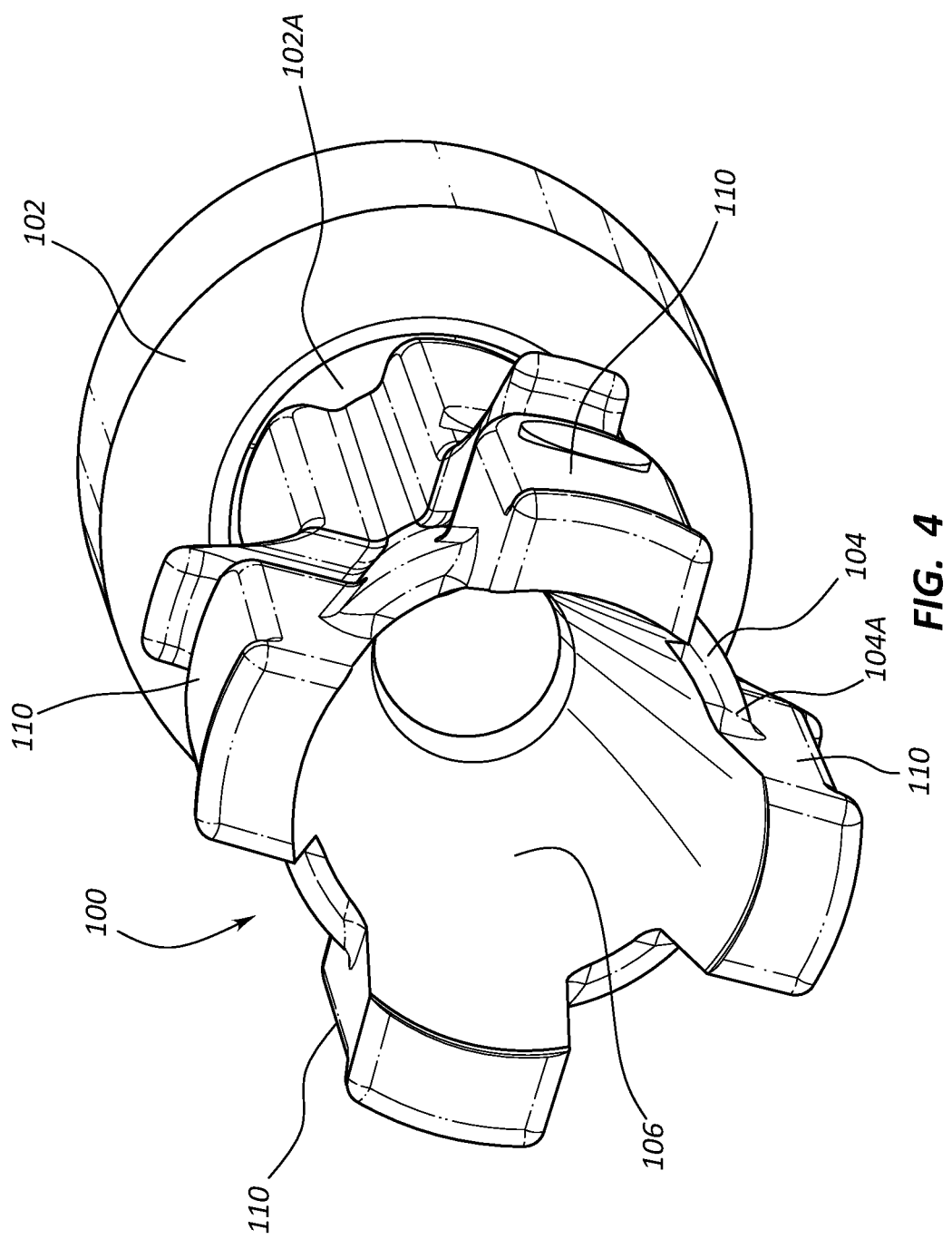
FIG. 4 is a perspective view of a blood control component of the catheter of FIG. 3.

FIGS. 4-5B depict various details of the blood control component 100, including an elongate body 104 extending between a proximal end 104A and a distal end 104B and defining a central conduit 106 through which fluids can flow. A plurality of ribs 110 is disposed on an outer surface of the body 104 such that the ribs longitudinally extend from proximally past the proximal end 104A of the body to the distal end 104B thereof. Each rib 110 radially extends from the body 104 to define a contoured profile along the longitudinal length thereof. The body 104 and ribs 110 contribute to generally define a conical shape to the blood control component 100. Deviations from the conical shape are also possible in other embodiments.

Each rib 110 further defines a notch 112 intermediately positioned along the longitudinal length of the rib, as well as a protrusion 114 at the proximal end of the rib. As seen in FIG. 3, the notch 112 of each rib 110 receives a portion of an annular ridge 120 defined on an inner surface of the catheter hub cavity 46A to keep the blood control component 100 in place within the cavity before actuation. Correspondingly, the protrusions 114 of each rib 110 engage with the annular ridge 120 when the blood control component 100 is actuated so as to prevent further distal movement thereof past its intended length of travel. The body 104 defines a channel 126 between adjacent ribs 110, thus providing four fluid flow channels in the illustrated embodiment. Note that in one embodiment one or more ribs 110 can be offset along the longitudinal length thereof such that a proximal portion of the rib including the protrusion 114 is not longitudinally aligned with (as in FIGS. 5A and 5B), but rather circumferentially offset from, a more distal portion of the rib.

FIGS. 6A-6C depict details of the blood control component 100 according to another embodiment, wherein the body 104 defines a plurality of channels 126 disposed about the conduit 106. An intermediate, annular shoulder 128 is also defined by the body 104.

Figure 7C:
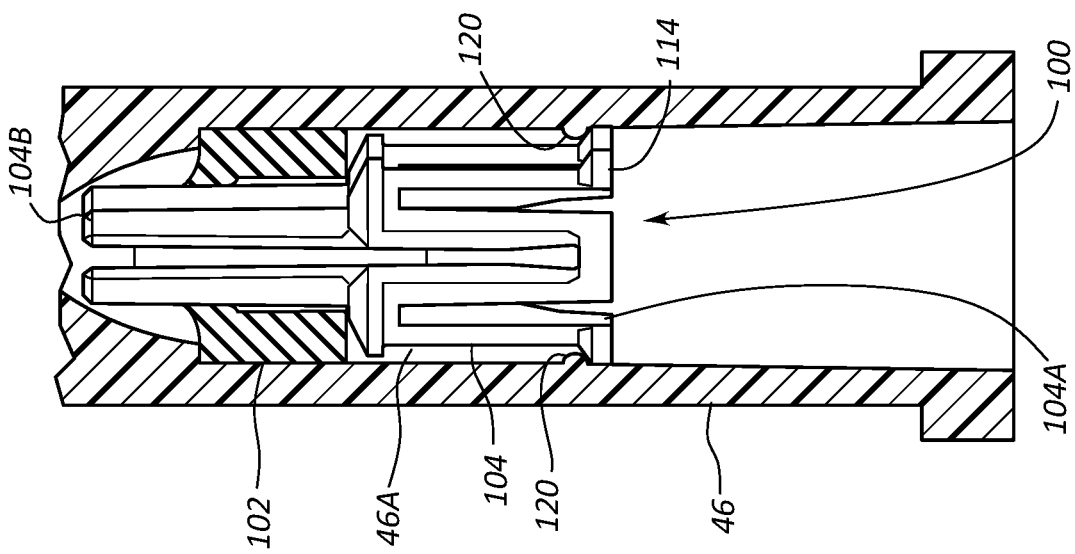
FIGS. 7A-7C show various views of use of the catheter and blood control catheter of FIGS. 6A-6C.
Figure 7B:
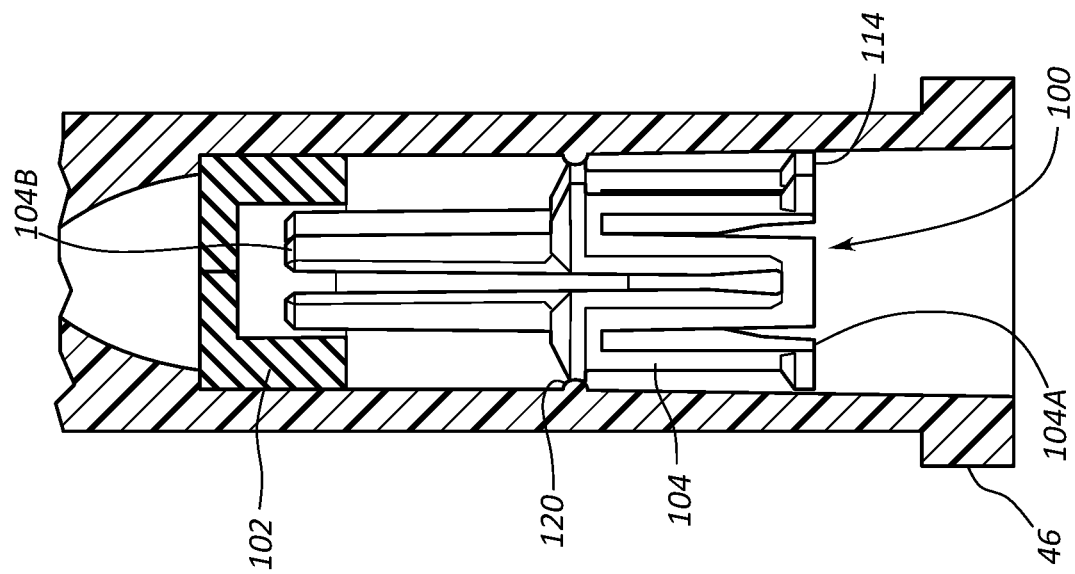
Figure 7A:
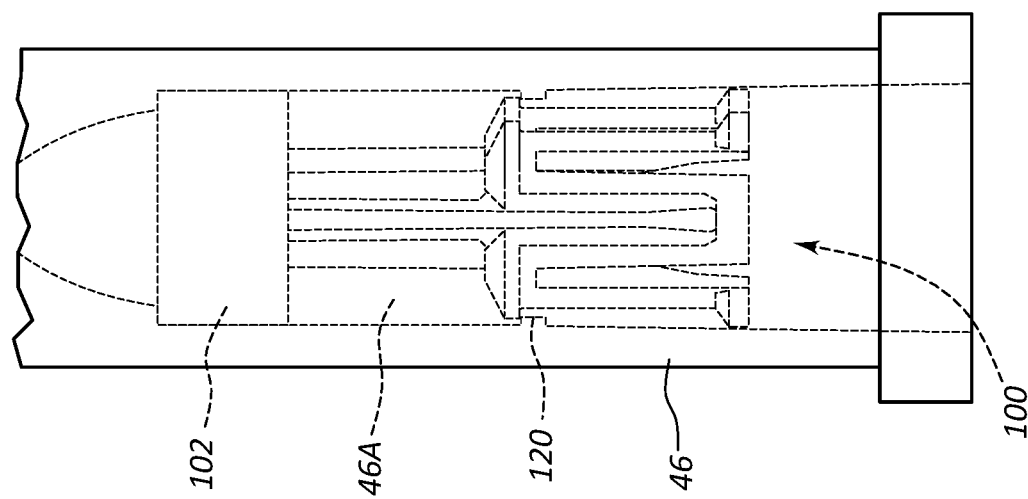

FIGS. 7A-7C depict various stages of operation of the blood control component 100 of FIGS. 6A-6C, though the principles described here also apply to the embodiment shown in FIGS. 4-5B as well. In particular, FIGS. 7A and 7B show the blood control component 100 in a relatively proximal position, also referred to herein as an un-actuated state, wherein the annular ridge 120 is received within the notches 112 (below the shoulders 128) of each rib 110 of the blood control component. In this position, the distal end 104B of the body 104 does not protrude through the valve 102 that is positioned distal to the blood control component and thus no fluid is able to pass through the catheter 42, as desired. The valve 102 in the closed position thus prevents blood leakage through the catheter 42, such as when the catheter has been placed within the patient but no external connection has been made to the catheter hub 46.

In contrast, FIG. 7C shows the blood control component 100 in a relatively distal position, also referred to herein as an actuated state, wherein the blood control component has been distally advanced (such as by insertion of a male luer connector into the catheter hub 46) such that the distal end 104B thereof has penetrated through the leaflets 102A of the valve 102, thus providing a fluid path through the valve via the conduit 106 of the blood control component. Further distal advancement of the blood control component 100 is prevented by engagement of the protrusions 114 against the annular ridge 120. As mentioned, the distal movement of the blood control component 100 is caused by the insertion into the catheter hub cavity 46A by a luer connector or other apparatus that can be operably connected to the catheter hub 46.

Figure 11:
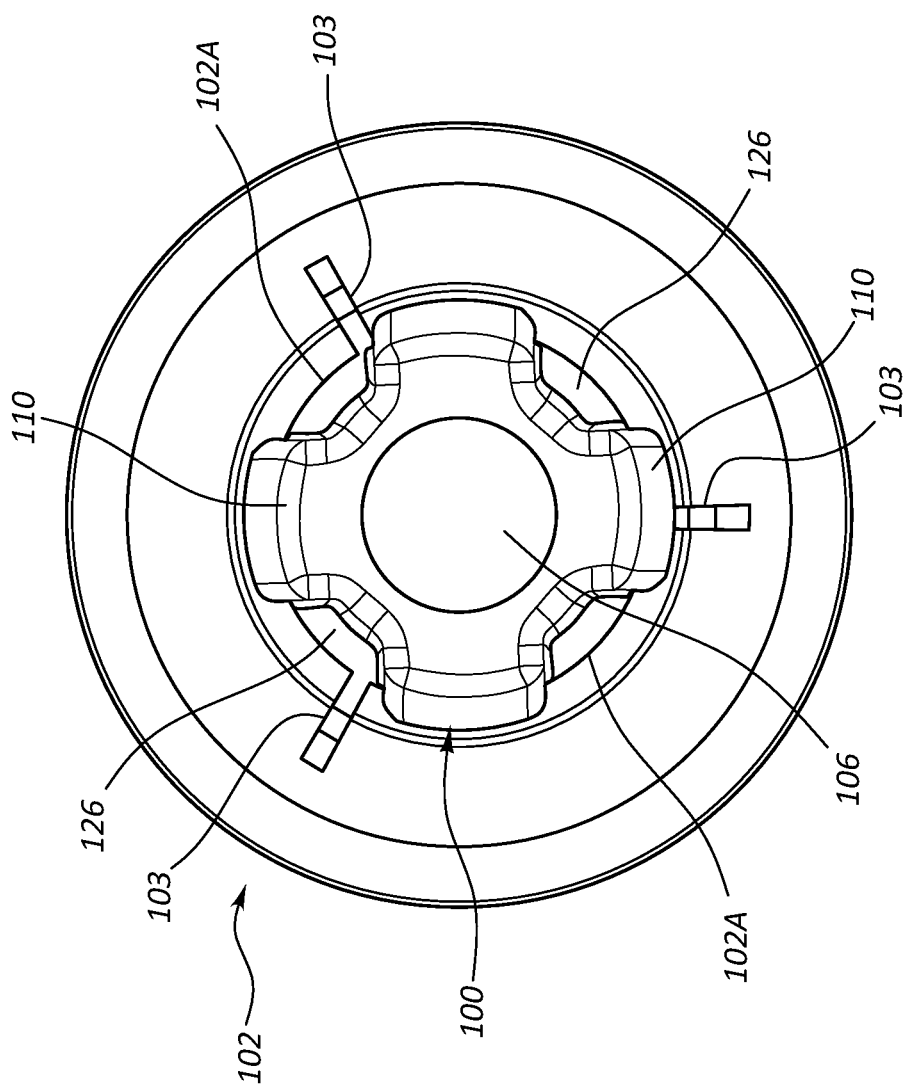
FIG. 11 is an isolation view showing the blood control component piercing the valve of the catheter insertion device of FIGS. 1A and 1B.

In accordance with the present embodiment, the blood control component 100 is configured to eliminate an entrapment zone between the blood control component and the valve 102 after the blood control component has pierced the valve in its actuated state. Specifically, and with respect to the embodiment shown in FIGS. 4-5B, the ribs 110 cause additional deformation of the leaflets 102A of the valve 102 when the blood control component pierces the valve, as seen in FIG. 11. This in turn prevents partial sealing of the leaflets 102A to the exterior surface of the blood control component body 104, thus providing spacing therebetween and additional fluid flow paths via the channels 126 between the exterior surface of the blood control component body 104 and the valve leaflets. Thus, fluid is able to flow through the catheter hub cavity 46A not only internal to the blood control component body 104 via the conduit 106 but also external to the blood control component body via the channels 126, which are made patent by the interaction of the ribs 110 with the valve leaflets 104A. This fluid flow external to the blood control component 100 assists in moving fluid through the entirety of the hub cavity 46A, thus desirably preventing fluid flow stagnation in the region between the blood control component 100 and the valve 102.

Note that in the present embodiment an outer termination point of each slit 103 that form the leaflets 102A defines a staggered termination point, as seen in FIG. 11. Note also that the ribs described herein are but one example of one or more extended surfaces that can be included with the blood control component to enable additional fluid flow channels to be defined on an outer surface of the blood control component to enable fluid flow about the exterior of the blood control component when the blood control component pierces the valve. Examples of other extended surfaces include bumps, annular surfaces, fins, etc. These and other embodiments are therefore contemplated.

The blood control component 100 of FIGS. 6A-6C operates similarly to that described immediately above in connection with FIGS. 4-5B, wherein the channels 126 provide fluid flow in addition to the conduit 106 so as to prevent fluid flow stagnation between the blood control component 100 and the valve 102.

FIGS. 8A-8F depict various details regarding the aforementioned needle hub 14 of the insertion device 10, which includes an elongate body 140 extending between a proximal end 140A and a distal end 140B. A slot 142 extends longitudinally along the length of the body 140 and is sized for receiving a portion of the length of the needle 16 therein. As mentioned, the ridge 144 is included on the proximal end 140A of the needle hub and provides a surface against which the spring 50 can act to retract the needle hub and attached needle 16 into the cavity of the housing 12. The slot 142 defines a volume 146 within which the above-described flash indicator 80 can be received.

Note that the slot 142 is configured so that differing sizes of needle can be received and affixed therein. To that end, the slot 142 includes three shoulders 148 to support the needle 16 within the slot 142. Note that the proximal edge of each of the shoulders 148 is relatively abrupt in shape so as to prevent spillage of a liquid epoxy adhesive that is placed in the slot 142 proximate the shoulders to secure the needle 16 within the slot.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A method of making a catheter assembly, comprising:
   forming a catheter, comprising:
     a catheter tube; and
     a catheter hub coupled to a proximal end of the catheter tube, the catheter hub including a valve and an annular ridge defined proximal of the valve;
   forming a fluid control component, comprising:
     a conduit fluidly connecting a proximal opening in a proximal end of the fluid control component to a distal opening in a distal end of the fluid control component; and
     a plurality of longitudinally extending ribs disposed on an exterior surface of the fluid control component, each of the ribs extending from the proximal end to the distal end, each of the plurality of longitudinally extending ribs comprising:
       a notch at an intermediate portion between the proximal end and the distal end, the notch engaging the annular ridge in a first position; and
       a protrusion at the proximal end configured to engage the annular ridge in a second position; and
   positioning the fluid control component into the catheter hub so that the fluid control component is movable between:
     the first position with the distal end positioned proximal of the valve; and
     the second position with the distal end positioned distal to the valve.

2. The method of making according to claim 1, wherein the valve includes a tricuspid valve including three slits.

3. The method of making according to claim 2, wherein an outer termination point of each slit is a staggered termination point.

4. The method of making according to claim 1, wherein each of the ribs includes a shoulder at an intermediate point between the proximal end and the distal end of the fluid control component.

5. The method of making according to claim 1, wherein the fluid control component has a generally conical shape.

6. The method of making according to claim 1, wherein the plurality of longitudinally extending ribs comprise four equally spaced longitudinally extending ribs around a circumference of the fluid control component.

7. The method of making according to claim 1, wherein each of the plurality of longitudinally extending ribs extend proximal of the proximal opening.

8. The method of making according to claim 1, wherein the fluid control component further comprises a fluid flow channel between each of the plurality of longitudinally extending ribs.

\* \* \* \* \*